US012778955B2

(12) United States Patent
Cassella

(10) Patent No.: US 12,778,955 B2
(45) Date of Patent: Nov. 3, 2026

(54) REGIMENS FOR THE TREATMENT OF HAIR LOSS DISORDERS WITH DEUTERATED JAK INHIBITORS

(71) Applicant: Sun Pharmaceutical Industries, Inc., Princeton, NJ (US)

(72) Inventor: James V. Cassella, Essex, CT (US)

(73) Assignee: Sun Pharmaceutical Industries, Inc., Princeton, NJ (US)

( * ) Notice: Subject to any disclaimer, the term of this patent is extended or adjusted under 35 U.S.C. 154(b) by 518 days.

(21) Appl. No.: 18/033,730

(22) PCT Filed: Oct. 28, 2021

(86) PCT No.: PCT/US2021/057123
§ 371 (c)(1),
(2) Date: Apr. 25, 2023

(87) PCT Pub. No.: WO2022/094133
PCT Pub. Date: May 5, 2022

(65) Prior Publication Data

US 2023/0390292 A1 Dec. 7, 2023

Related U.S. Application Data

(60) Provisional application No. 63/155,637, filed on Mar. 2, 2021, provisional application No. 63/106,790, filed on Oct. 28, 2020.

(51) Int. Cl.
*A61K 31/519* (2006.01)
*A61K 9/20* (2006.01)
*A61P 17/14* (2006.01)

(52) U.S. Cl.
CPC .............. *A61K 31/519* (2013.01); *A61K 9/20* (2013.01); *A61P 17/14* (2018.01)

(58) Field of Classification Search
CPC .................................................... A61K 31/519
See application file for complete search history.

(56) References Cited

U.S. PATENT DOCUMENTS 7,014,866 B2 3/2006 Infeld et al.
8,754,224 B2 6/2014 Hurter et al.
9,000,161 B2 4/2015 Zhou et al.
9,249,149 B2 2/2016 Silverman et al.
10,561,659 B2 * 2/2020 Wagner ................ A61K 9/2013
12,076,323 B2 * 9/2024 Wagner ................... A61P 17/14
12,285,432 B2 * 4/2025 Cassella .................. A61P 17/14
12,364,699 B2 * 7/2025 Brummel ............. A61K 9/2054
2006/0079502 A1 4/2006 Lang
2006/0094744 A1 5/2006 Maryanoff et al.

FOREIGN PATENT DOCUMENTS

WO WO-2017/192905 A1 11/2017
WO 2020/163653 A1 8/2020
WO WO-2022/094133 A1 5/2022
WO WO-2022/094133 A9 5/2022

OTHER PUBLICATIONS

Anisel et.al. "Pharmaceutical Dosage Forms and Drug Delivery Systems" 7th edition, 1999 (Year: 1999).*
International Search Report and Written Opinion for International Application No. PCT/US2021/057123 mailed Feb. 7, 2022.
Olsen et al., "Ruxolitinib cream for the treatment of patients with alopecia areata: A 2-part, double-blind, randomized, vehicle-controlled phase 2 study," J Am Acad Dermatol, 82(2): 412-419 (2019).
Rosmarin et al., "Ruxolitinib cream for treatment of vitiligo: a randomised, controlled, phase 2 trial," Lancet, 396(10244): 110-120 (2020).
Gannes et al., "Natural abundance variations in stable isotopes and their potential uses in animal physiological ecology," Comparative Biochemistry and Physiology Part A: Molecular & Integrative Physiology 119(3):725-737 (1998).
Wada and Hanba, "Natural abundance of carbon, nitrogen, and hydrogen isotope ratios in biogenic substances: present and future," Seikagaku. The Journal of Japanese Biochemical Society 66(1):15-29 (1994). Machine Translation of Abstract.
Jahn-Bassler K et al.: "Sequential high- and low-dose systemic corticosteroid therapy for severe childhood alopecia areata"; J Dtsch Dermatol Ges, vol. 15, No. 1, pp. 42-47, DOI: 10.1111/ddg.12875, Jan. 31, 2017 (Jan. 31, 2017).

* cited by examiner

*Primary Examiner* — John S Kenyon
*Assistant Examiner* — Rehana Ismail
(74) *Attorney, Agent, or Firm* — Medler Ferro Woodhouse & Mills PLLC

(57) ABSTRACT

Disclosed is a method of treating in a subject hair loss disorders that are beneficially treated by administering a JAK1 and/or JAK2 inhibitor. The method comprises administering to the subject an effective amount of Compound (I): or a pharmaceutically acceptable salt thereof.

Compound (I)

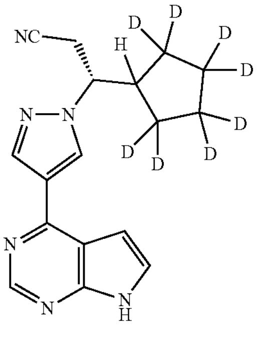

20 Claims, 8 Drawing Sheets

REGIMENS FOR THE TREATMENT OF HAIR LOSS DISORDERS WITH DEUTERATED JAK INHIBITORS

RELATED APPLICATIONS

This application is the U.S. National Stage of International Application No. PCT/US2021/057123, filed Oct. 28, 2021, which designates the U.S., published in English, and claims the benefit of U.S. Provisional Application No. 63/106,790, filed on Oct. 28, 2020 and U.S. Provisional Application No. 63/155,637, filed on Mar. 2, 2021. The entire teachings of the above applications are incorporated herein by reference.

BACKGROUND OF THE INVENTION

Alopecia areata (AA) is an autoimmune disease that results in partial or complete loss of hair on the scalp and body. The scalp is the most commonly affected area, but any hair-bearing site can be affected alone or together with the scalp. Up to 650,000 patients are affected with alopecia areata (AA) in the U.S. at any given time, including men, women, and children. AA profoundly impacts patients; AA is associated with serious psychological consequences, including anxiety and depression, and with other autoimmune conditions.

There is no known cure for AA. Improved treatments for AA and other hair loss disorders are needed.

SUMMARY OF THE INVENTION

It has now been found that deuterated analogs of ruxolitinib (including Compound (I), also referred to as (R)-3-(4-(7H-pyrrolo[2,3-d]pyrimidin-4-yl)-1H-pyrazol-1-yl)-3-(cyclopentyl-2,2,3,3,4,4,5,5-$d_8$)propanenitrile, or D8-ruxolitinib, or CTP-543), are useful for the treatment of hair-loss disorders, including alopecia areata. Published PCT Application No. WO17/192905 describes the use of CTP-543 for the treatment of alopecia areata. Compound (I) is represented by the following structural formula:

Compound (I)

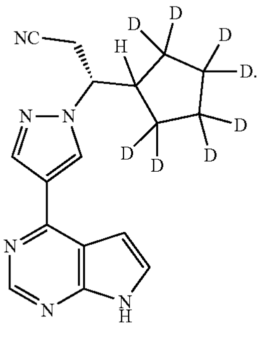

In certain embodiments, Compound (I) is administered as a pharmaceutically acceptable salt, such as the phosphate salt. Compound (I) can be administered in doses in the range of about 8 mg to about 32 mg per day (or the equivalent weight based on a salt, such as Compound (I) phosphate salt), administered as a single daily dose or in divided doses (e.g., twice per day). Based on these discoveries, novel therapies using Compound (I) or a pharmaceutically acceptable salt thereof, for treating a hair loss disorder in a mammalian subject are disclosed herein.

In one aspect, the invention provides a method of treating a hair loss disorder in a human subject, the method comprising administering to the subject a compound represented by the following structural formula:

Compound (I)

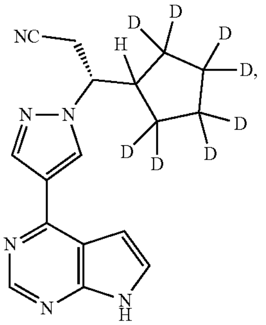

wherein each position designated specifically as deuterium has at least 95% incorporation of deuterium; or a pharmaceutically acceptable salt thereof; wherein the compound, or pharmaceutically acceptable salt thereof, is administered for (1) a first period of 8-24 weeks in an amount in the range of about 8 mg to about 32 mg per day, followed by (2) a second period of at least 8 weeks wherein the compound, or pharmaceutically acceptable salt thereof, is administered in an amount per day that is 50 to 75 percent of the amount per day administered during the first period, such that the hair loss disorder is treated.

In certain embodiments, the hair loss disorder is alopecia areata.

In certain embodiments, in the first period, the compound, or a pharmaceutically acceptable salt thereof, is administered at about 12 mg/day, about 16 mg/day, about 24 mg/day, or about 32 mg per day.

In certain embodiments, in the second period, the compound, or a pharmaceutically acceptable salt thereof, is administered at about 6 mg/day, about 8 mg/day, about 12 mg/day, or about 16 mg per day.

In certain embodiments, in the first period, the compound, or a pharmaceutically acceptable salt thereof, is administered at about 24 mg/day, and in the second period, the compound, or a pharmaceutically acceptable salt thereof, is administered at about 16 mg/day. In certain embodiments, the about 24 mg/day of the compound or salt is administered once per day, and the about 16 mg/day of the compound or salt is administered once per day. In certain embodiments, the about 24 mg/day of the compound or salt is administered as about 12 mg twice per day, and the about 16 mg/day of the compound or salt is administered as about 8 mg twice per day.

In certain embodiments, in the first period, the compound, or a pharmaceutically acceptable salt thereof, is administered at about 16 mg/day, and in the second period, the compound, or a pharmaceutically acceptable salt thereof, is administered at about 8 mg/day. In certain embodiments, the about 16 mg/day of the compound or salt is administered once per day, and the about 8 mg/day of the compound or salt is administered once per day. In certain embodiments, the about 16 mg/day of the compound or salt is administered as about 8 mg twice per day, and the about 8 mg/day of the compound or salt is administered as about 4 mg twice per day.

In certain embodiments, the compound, or a pharmaceutically acceptable salt thereof, is administered orally.

In certain embodiments, the compound, or a pharmaceutically acceptable salt thereof, is administered in a pharmaceutical formulation which is a tablet.

In certain embodiments, the compound, or a pharmaceutically acceptable salt thereof, is administered once per day in the first period. In certain embodiments, the compound, or a pharmaceutically acceptable salt thereof, is administered twice per day in the first period.

In certain embodiments, the compound, or a pharmaceutically acceptable salt thereof, is administered once per day in the second period. In certain embodiments, the compound, or a pharmaceutically acceptable salt thereof, is administered twice per day in the second period.

In certain embodiments, the first period is about 8-24 weeks. In certain embodiments, the first period is about 12 weeks. In certain embodiments, the first period is about 16 weeks. In certain embodiments, the first period is about 20 weeks. In certain embodiments, the first period is about 24 weeks. In certain embodiments, the second period is at least 12 weeks. In certain embodiments, the second period is at least 24 weeks.

In certain embodiments, the first period is about 8-12 weeks. In certain embodiments, the first period is about 8 weeks. In certain embodiments, the first period is about 12 weeks. In certain embodiments, the first period is at least 8 weeks.

In certain embodiments, in Compound (I), each position designated specifically as deuterium has at least 97% incorporation of deuterium.

Another aspect of the invention is Compound (I), or a pharmaceutically acceptable salt thereof (i.e., an equivalent amount of a pharmaceutically acceptable salt, such as the phosphate salt), for use in treating hair loss disorders that can be treated by compounds that can be treated by compounds that modulate the activity of Janus Associated Kinase 1 (JAK1) and/or Janus Associated Kinase 2 (JAK2). The compound may be administered at the dosing regimens disclosed herein. In certain embodiments, the hair loss disorder is alopecia areata.

Still another aspect of the invention is the use of Compound (I), or a pharmaceutically acceptable salt thereof (i.e., an equivalent amount of a pharmaceutically acceptable salt, such as the phosphate salt), for the manufacture of a medicament for treating hair loss disorders that can be treated by compounds that modulate the activity of Janus Associated Kinase 1 (JAK1) and/or Janus Associated Kinase 2 (JAK2). The compound may be administered at the dosing regimens disclosed herein. In certain embodiments, the hair loss disorder is alopecia areata.

DETAILED DESCRIPTION OF THE INVENTION

Definitions

Figure 1:
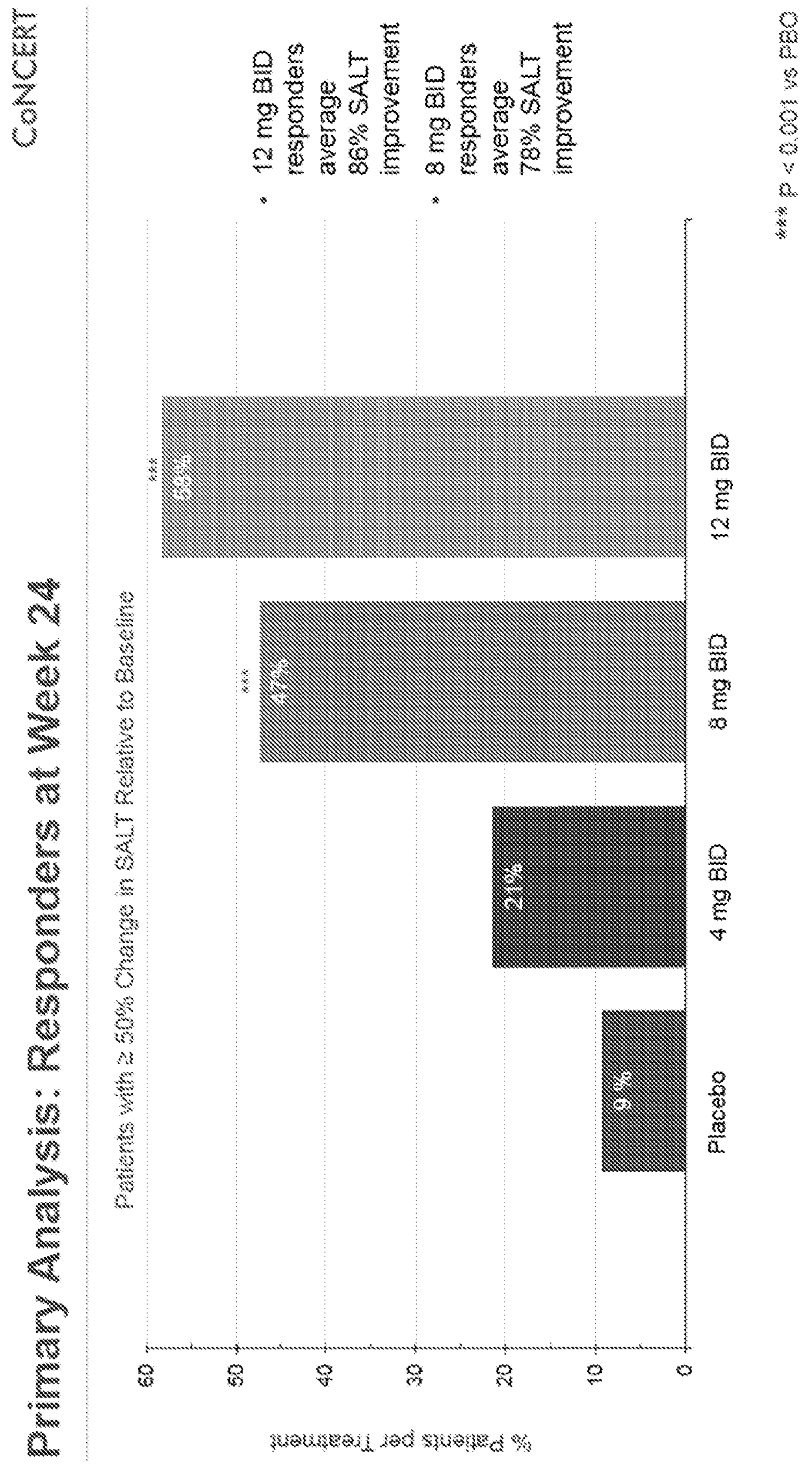
FIG. 1 shows the percentage of responders at week 24 of a Phase 2a trial (patients with ≥50% reduction in SALT score relative to baseline), including placebo, 4 mg BID, 8 mg BID, and 12 mg BID cohorts.
Figure 2:
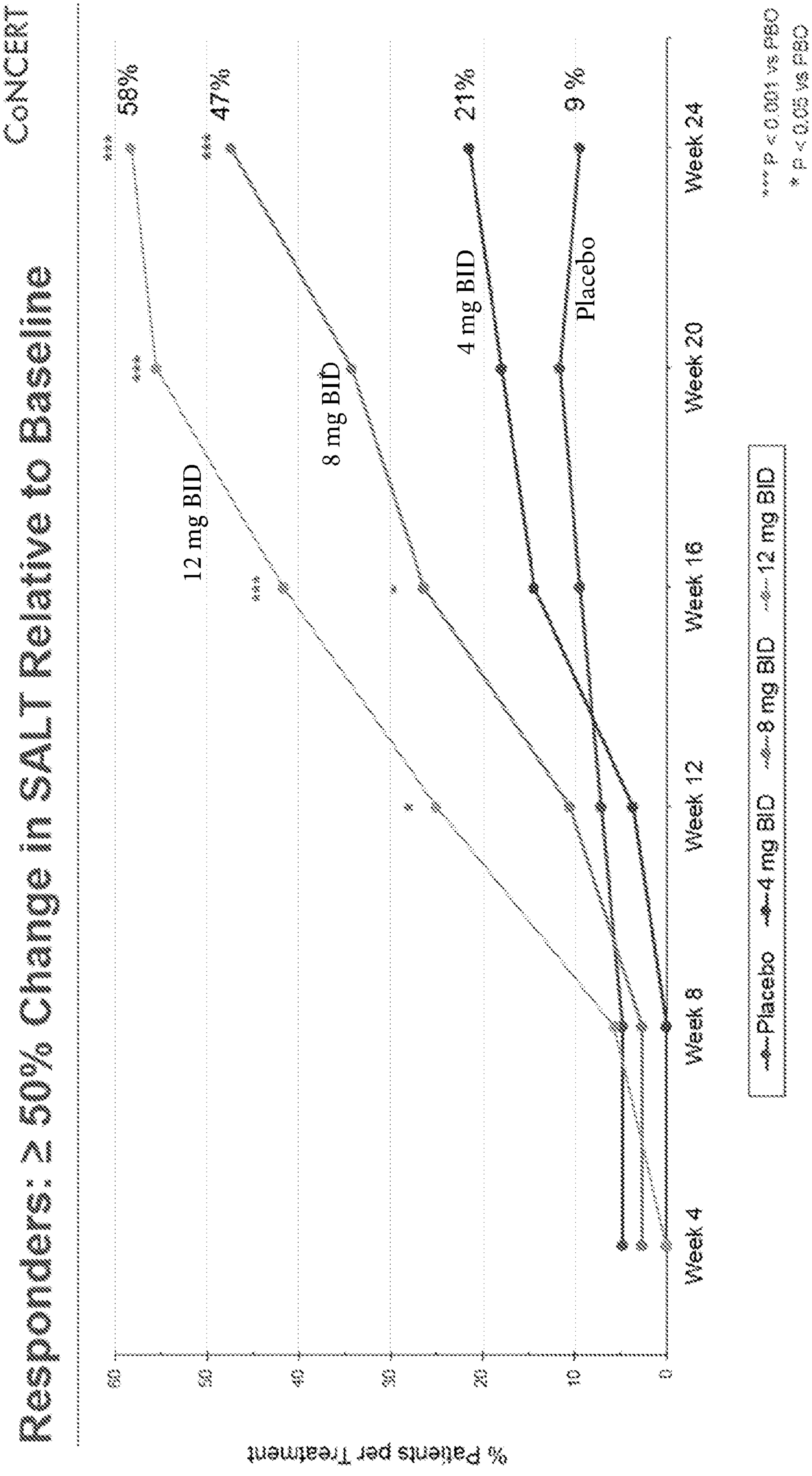
FIG. 2 shows the percentage of responders (patients with ≥50% reduction in SALT score relative to baseline) by visit in the Phase 2a trial, including placebo, 4 mg BID, 8 mg BID, and 12 mg BID cohorts.
Figure 3:
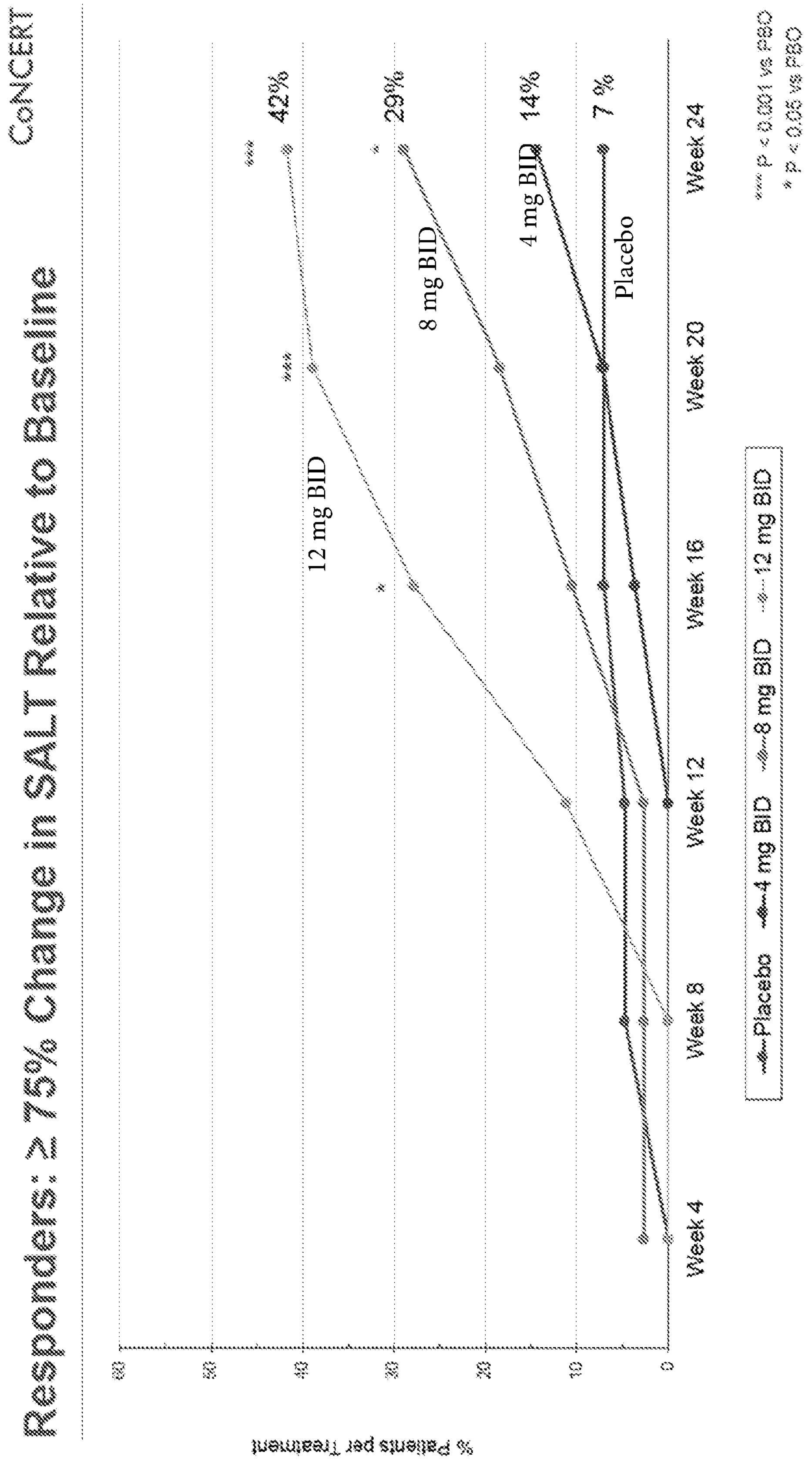
FIG. 3 shows the percentage of responders (patients with ≥75% reduction in SALT score relative to baseline) by visit in the Phase 2a trial, including placebo, 4 mg BID, 8 mg BID, and 12 mg BID cohorts.
Figure 4:
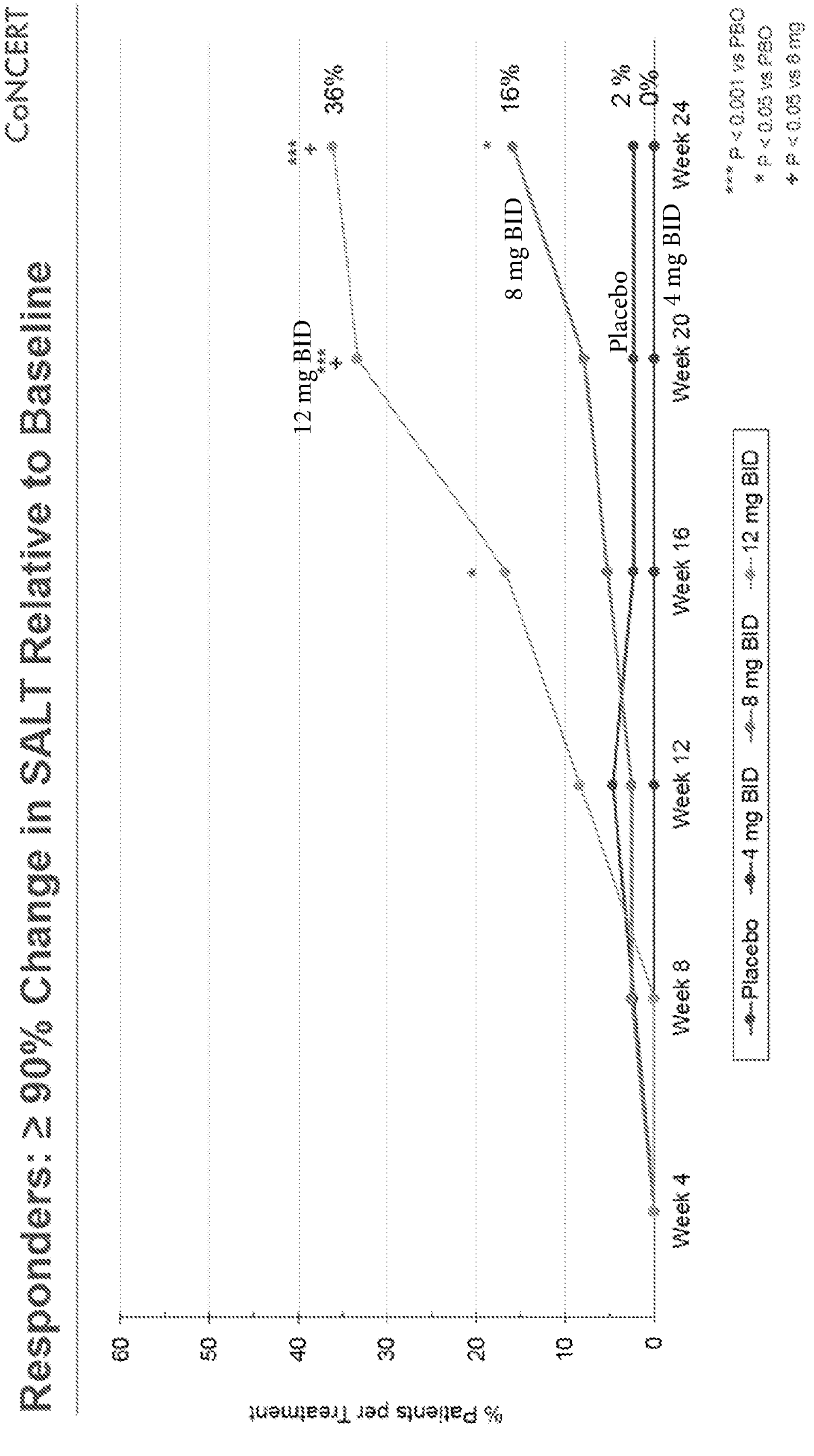
FIG. 4 shows the percentage of responders (patients with ≥90% reduction in SALT score relative to baseline) by visit in the Phase 2a trial, including placebo, 4 mg BID, 8 mg BID, and 12 mg BID cohorts.
Figure 5:
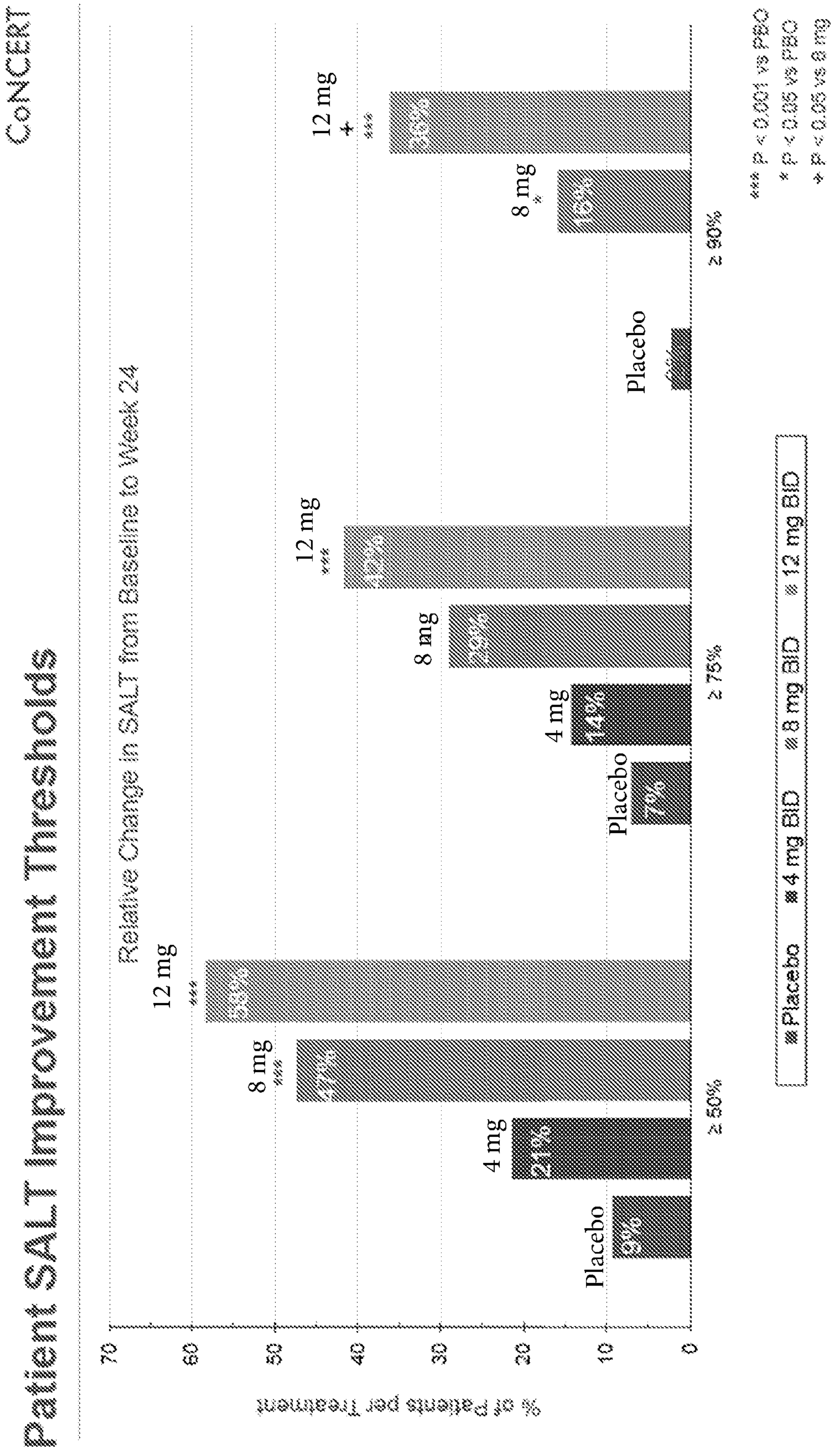
FIG. 5 shows patient SALT score improvement after 24 weeks of the Phase 2a trial, including placebo, 4 mg BID, 8 mg BID, and 12 mg BID cohorts.
Figure 6:
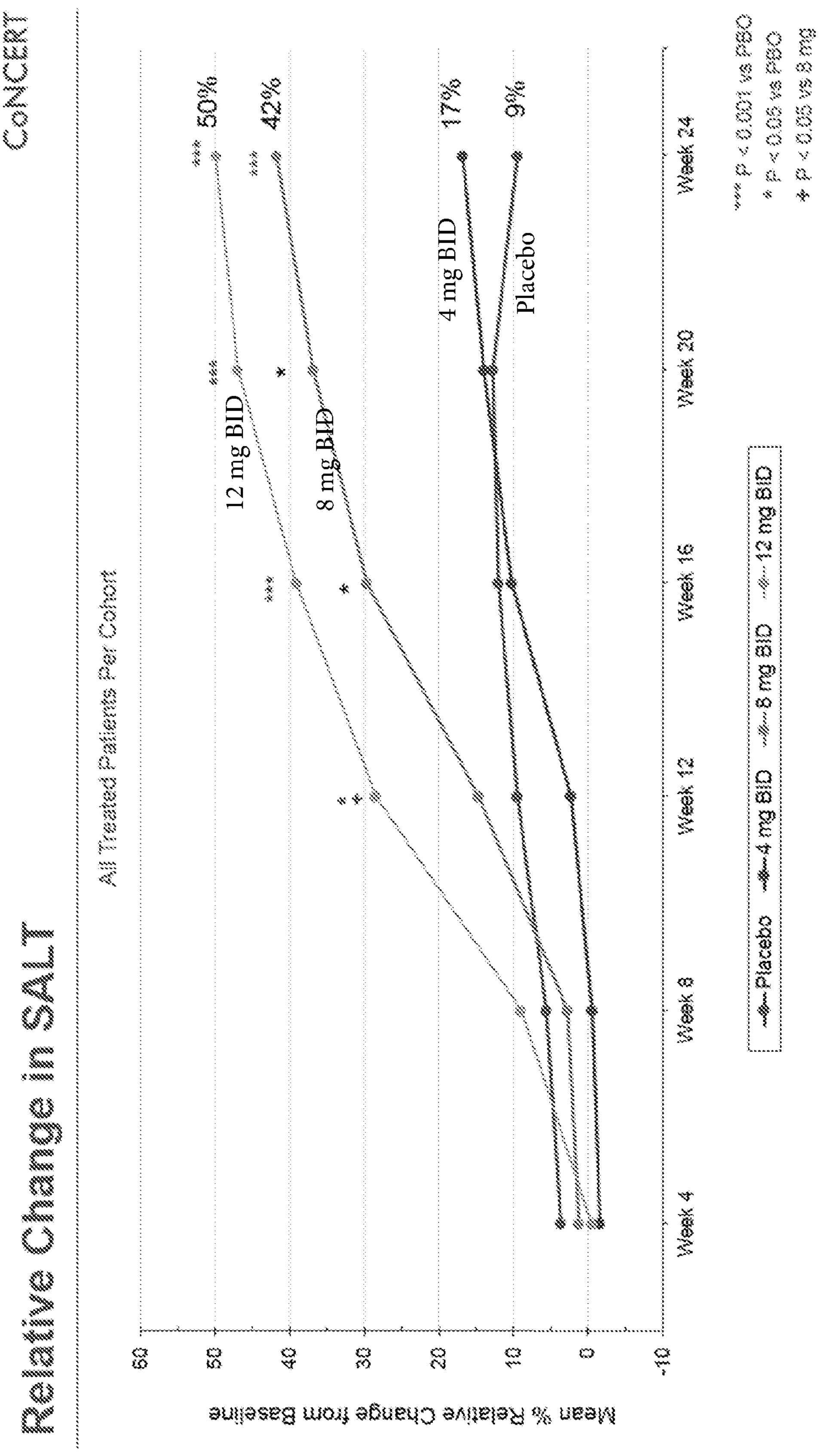
FIG. 6 shows the relative change in SALT score by visit in the Phase 2a trial, including placebo, 4 mg BID, 8 mg BID, and 12 mg BID cohorts.

The term "treat" means decrease, suppress, attenuate, diminish, arrest, or stabilize the development or progression of a disease (e.g., a disease or disorder delineated herein), lessen the severity of the disease or improve the symptoms associated with the disease. For example, treatment of a hair loss disorder includes regrowth of hair, prevention of further hair loss, or diminishing the rate of hair loss.

"Hair loss disorder" means any condition or disorder that results in loss of hair on one or more areas of the body. Hair loss disorders include, without limitation, androgenetic alopecia, alopecia areata, telogen effluvium, alopecia areata, alopecia totalis, and alopecia universalis.

The efficacy of treatment of hair loss disorders such as alopecia areata can be measured in a variety of ways, some of which are known in the art. For example, the "severity of alopecia tool", otherwise known as SALT, is a validated assessment scale developed by the National Alopecia Areata Foundation working committee—to evaluate the degree of hair loss. See, e.g., Olsen E A, Hordinsky M K, Price V H, et al. Alopecia areata investigational assessment guidelines—Part II. J Am Acad Dermatol 2004: 51: 440-447 (incorporated herein by reference). The SALT score is calculated for a patient by measuring the percentage of hair loss in each of the 4 areas of the scalp and adding the total to achieve a composite score. Hair regrowth is reflected by a decrease in the SALT score. For example, no hair on the scalp would have a SALT score of 100 while complete hair regrowth would be a SALT score of 0. In certain embodiments, methods of treatment as described herein can provide a SALT score improvement of at least 10 points after treatment (for example, from a SALT score of 100 prior to treatment to a SALT score of 90 after treatment). In further embodiments, methods of treatment as described herein can provide a SALT score improvement of at least 20 points, 30 points, 40 points, 50 points, 60 points, 70 points, 80 points, 90 points, or 100 points. In certain embodiments, methods of treatment as described herein can provide after treatment at least a 20% improvement from baseline in the patient's SALT score, or at least a 30% improvement from baseline in the patient's SALT score, or at least a 40% improvement from baseline in the patient's SALT score, or at least a 50% improvement from baseline in the patient's SALT score, or at least a 60% improvement from baseline in the patient's SALT score, or at least a 70% improvement from baseline in the patient's SALT score, or at least a 75% improvement from baseline in the patient's SALT score or at least a 80% improvement from baseline in the patient's SALT score, or at least a 90% improvement from baseline in the patient's SALT score.

The term "subject", as used herein, includes humans, as well as non-human mammals such as cats, dogs, sheep, cattle, pigs, goats, non-human primates (including monkeys and apes) and the like.

The term "about", as used herein, means "approximately," that is, within an acceptable error range for the particular value as determined by one of ordinary skill in the art. For example, "about" can mean a range of up to 10% above or below the particular value, up to 5% above or below the particular value, or up to 1% above or below the particular value. In addition, when the particular value is a length of time in weeks, the term "about" can mean up to two weeks more or less, or one week more or less.

It will be recognized that some variation of natural isotopic abundance occurs in a synthesized compound depending upon the origin of chemical materials used in the synthesis. Thus, a preparation of ruxolitinib will inherently contain small amounts of deuterated isotopologues. The concentration of naturally abundant stable hydrogen and carbon isotopes, notwithstanding this variation, is small and immaterial as compared to the degree of stable isotopic substitution of compounds of this invention. See, for instance, Wada, E et al., Seikagaku, 1994, 66:15; Gannes, L Z et al., Comp Biochem Physiol Mol Integr Physiol, 1998, 119:725.

In Compound (I), any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. However, in certain embodiments where stated, when a position is designated specifically as "H" or "hydrogen", the position has at least 80%, at least 90%, at least 95%, at least 96%, at least 97%, at least 98%, or at least 99% hydrogen. In some embodiments, where specifically stated, when a position is designated specifically as "H" or "hydrogen", the position incorporates ≤20% deuterium, ≤10% deuterium, ≤5% deuterium, ≤4% deuterium, ≤3% deuterium, ≤2% deuterium, or ≤1% deuterium. Also, unless otherwise stated, when a position is designated specifically as "D" or "deuterium", the position is understood to have deuterium at an abundance that is at least 3340 times greater than the natural abundance of deuterium, which is 0.015% (i.e., at least 50.1% incorporation of deuterium). The amount of deuterium incorporation at a designated position may be measured by analytical methods known to one of ordinary skill in the art, for example, by proton NMR.

The term "isotopic enrichment factor" as used herein means the ratio between the isotopic abundance and the natural abundance of a specified isotope.

In other embodiments, Compound (I) has an isotopic enrichment factor for each designated deuterium position (or atom) of at least 3500 (52.5% deuterium incorporation at each designated deuterium position), at least 4000 (60% deuterium incorporation), at least 4500 (67.5% deuterium incorporation), at least 5000 (75% deuterium), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

In some embodiments, in a compound of this invention, each designated deuterium position (or atom) has deuterium incorporation of at least 52.5%. In some embodiments, in a compound of this invention, each designated deuterium position has deuterium incorporation of at least 60%. In some embodiments, in a compound of this invention, each designated deuterium position has deuterium incorporation of at least 67.5%. In some embodiments, in a compound of this invention, each designated deuterium position has deuterium incorporation of at least 75%. In some embodiments, in a compound of this invention, each designated deuterium position has deuterium incorporation of at least 80%. In some embodiments, in a compound of this invention, each designated deuterium position has deuterium incorporation of at least 85%. In some embodiments, in a compound of this invention, each designated deuterium position has deuterium incorporation of at least 90%. In some embodiments, in a compound of this invention, each designated deuterium position has deuterium incorporation of at least 95%. In some embodiments, in a compound of this invention, each designated deuterium position has deuterium incorporation of at least 97%. In some embodiments, in a compound of this invention, each designated deuterium position has deuterium incorporation of at least 98%. In some embodiments, in a compound of this invention, each designated deuterium position has deuterium incorporation of at least 99%. In some embodiments, in a compound of this invention, each designated deuterium position has deuterium incorporation of at least 99.5%.

The term "isotopologue" refers to a molecule in which the chemical structure differs from the structure shown for Compound (I) only in the isotopic composition thereof.

The term "compound," when referring to a compound of this invention, refers to a collection of molecules having an identical chemical structure, except that there may be isotopic variation among the constituent atoms of the molecules. Thus, it will be clear to those of skill in the art that while Compound (I) is represented by a particular chemical structure having deuterium atoms at eight designated positions, Compound (I) will contain molecules having deuterium at each of the eight designated positions, and may also contain isotopologues having hydrogen atoms at one or more of the designated deuterium positions in that structure. The relative amount of such isotopologues in Compound (I) will depend upon a number of factors including the isotopic purity of deuterated reagents used to make the compound and the efficiency of incorporation of deuterium in the various synthesis steps used to prepare the compound. In certain embodiments, the relative amount of such isotopologues in toto will be less than 49.9% of the compound. In other embodiments, the relative amount of such isotopologues in toto will be less than 47.5%, less than 40%, less than 32.5%, less than 25%, less than 17.5%, less than 10%, less than 5%, less than 3%, less than 1%, or less than 0.5% of the compound.

The invention also provides salts of Compound (I). A salt of a compound of this invention is formed between an acid and a basic group of the compound, such as an amino functional group, or a base and an acidic group of the compound, such as a carboxyl functional group. According to another embodiment, the compound is a pharmaceutically acceptable acid addition salt, such as a phosphate salt.

The term "pharmaceutically acceptable," as used herein, refers to a component that is, within the scope of sound medical judgment, suitable for use in contact with the tissues of humans and other mammals without undue toxicity, irritation, allergic response and the like, and are commensurate with a reasonable benefit/risk ratio. A "pharmaceutically acceptable salt" means any non-toxic salt that, upon administration to a recipient, is capable of providing, either directly or indirectly, a compound of this invention. A "pharmaceutically acceptable counterion" is an ionic portion of a salt that is not toxic when released from the salt upon administration to a recipient.

Acids commonly employed to form pharmaceutically acceptable salts include inorganic acids such as hydrogen bisulfide, hydrochloric acid, hydrobromic acid, hydroiodic acid, sulfuric acid and phosphoric acid, as well as organic acids such as para-toluenesulfonic acid, salicylic acid, tartaric acid, bitartaric acid, ascorbic acid, maleic acid, besylic acid, fumaric acid, gluconic acid, glucuronic acid, formic acid, glutamic acid, methanesulfonic acid, ethanesulfonic acid, benzenesulfonic acid, lactic acid, oxalic acid, para-bromophenylsulfonic acid, carbonic acid, succinic acid, citric acid, benzoic acid and acetic acid, as well as related inorganic and organic acids. Such pharmaceutically acceptable salts thus include sulfate, pyrosulfate, bisulfate, sulfite, bisulfate, phosphate, monohydrogenphosphate, dihydrogenphosphate, metaphosphate, pyrophosphate, chloride, bromide, iodide, acetate, propionate, decanoate, caprylate, acrylate, formate, isobutyrate, caprate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, terephthalate, sulfonate, xylene sulfonate, phenylacetate, phenylpropionate, phenylbutyrate, citrate, lactate, β-hydroxybutyrate, glycolate, maleate, tartrate, methanesulfonate, propanesulfonate, naphthalene-1-sulfonate, naphthalene-2-sulfonate, mandelate and other salts. In one embodiment, pharmaceutically acceptable acid addition salts include those formed with mineral acids such as hydrochloric acid and hydrobromic acid, and especially those formed with organic acids such as maleic acid.

The term "stable compounds," as used herein, refers to compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

"D" and "d" both refer to deuterium. "Stereoisomer" refers to both enantiomers and diastereomers. "Tert" and "t-" each refer to tertiary. "US" refers to the United States of America.

"Substituted with deuterium" refers to the replacement of one or more hydrogen atoms with a corresponding number of deuterium atoms.

It has now been found that administration of Compound (I), or an equivalent amount of a pharmaceutically acceptable salt thereof, can result in hair growth after a first period of administration. According to this invention, the amount of Compound (I) or salt thereof to be administered to a patient or subject can then (after the first period of administration) be reduced for a second period of treatment, while maintaining and/or extending (increasing) hair growth achieved during the first period. In general, the amount of Compound (I) or salt thereof that is administered in the second period is sufficient to maintain hair growth achieved during the first period (e.g., as measured by the severity of alopecia tool (SALT) score), e.g., is about 50 to 75 percent of the amount per day administered during the first period (e.g., if 16 mg/day of Compound (I) or salt thereof is administered during the first period, 8 to 12 mg/day can be administered in the second period). In certain embodiments, the maintenance dose (the amount per day administered during the second period) is about 33.3% of the amount per day administered during the first period.

In one aspect, the invention provides a method of treating a hair loss disorder in a human subject, the method comprising administering to the subject a compound represented by the following structural formula:

Compound (I)

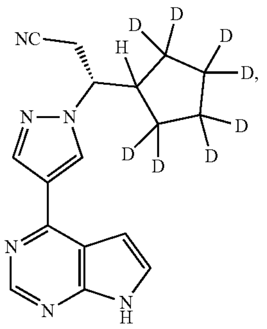

or a pharmaceutically acceptable salt thereof; wherein each position designated specifically as deuterium has at least 90% incorporation of deuterium; wherein the compound, or pharmaceutically acceptable salt thereof, is administered for (1) a first period wherein the compound, or pharmaceutically acceptable salt thereof, is administered in an amount in the range of 8 mg to 32 mg per day, followed by (2) a second period wherein the compound, or pharmaceutically acceptable salt thereof, is administered in an amount per day that is 50 to 75 percent of the amount per day administered during the first period, such that the hair loss disorder is treated. In certain embodiments, the first period is about 8-24 weeks, e.g., 8 weeks, 12 weeks, 16 weeks, 20 weeks, or 24 weeks. In certain embodiments, the second period is at least 8 weeks, e.g., 8 weeks, 12 weeks, 16 weeks, 20 weeks, or 24 weeks (or longer).

In one aspect, the invention provides a method of treating a hair loss disorder in a human subject, the method comprising administering to the subject a compound represented by the following structural formula:

Compound (I)

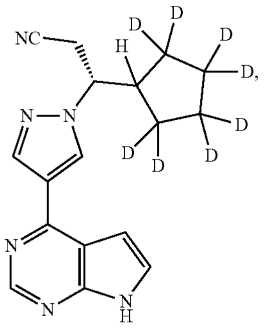

or a pharmaceutically acceptable salt thereof; wherein each position designated specifically as deuterium has at least 95% incorporation of deuterium; wherein the compound, or pharmaceutically acceptable salt thereof, is administered for (1) a first period wherein the compound, or pharmaceutically acceptable salt thereof, is administered in an amount in the range of 8 mg to 32 mg per day, followed by (2) a second period wherein the compound, or pharmaceutically acceptable salt thereof, is administered in an amount per day that is 50 to 75 percent of the amount per day administered during the first period, such that the hair loss disorder is treated. In certain embodiments, the first period is about 8-24 weeks, e.g., 8 weeks, 12 weeks, 16 weeks, 20 weeks, or 24 weeks. In certain embodiments, the second period is at least 8 weeks, e.g., 8 weeks, 12 weeks, 16 weeks, 20 weeks, or 24 weeks (or longer).

In certain embodiments, the hair loss disorder is treated when there is a ≥50% change in the subject's SALT score at the end of the first period relative to the subject's baseline SALT score prior to treatment. In certain embodiments, the hair loss disorder is treated when the subject's SALT score is less than or equal to 20 at the end of the second period. In certain embodiments, the hair loss disorder is treated when there is a ≥50% change in the subject's SALT score at the end of the first period relative to the subject's baseline SALT score prior to treatment, and the subject's SALT score is less than or equal to 20 at the end of the second period.

In certain embodiments, the length of the first period is sufficient to achieve a SALT score at the end of the first period of less than or equal to 50, less than or equal to 40, less than or equal to 30, less than or equal to 20, less than or equal to 15, less than or equal to 10, less than or equal to 5, less than or equal to 1, or zero. In certain embodiments, the length of the first period is sufficient to achieve a SALT score at the end of the first period of less than or equal to 20. In certain embodiments, the length of the first period is sufficient to achieve a SALT score at the end of the first period of less than or equal to 15. In certain embodiments, the length of the first period is sufficient to achieve a SALT score at the end of the first period of less than or equal to 10. In certain embodiments, the length of the first period is sufficient to achieve a SALT score at the end of the first period of less than or equal to 5. In certain embodiments, the length of the first period is sufficient to achieve a SALT score at the end of the first period of less than or equal to 1. In certain embodiments, the length of the first period is sufficient to achieve a SALT score at the end of the first period of zero.

In certain embodiments, the hair loss disorder is alopecia areata.

In certain embodiments, in the first period, the compound, or a pharmaceutically acceptable salt thereof, is administered at about 8 mg/day, about 12 mg/day, about 16 mg/day, about 24 mg/day, or about 32 mg per day.

In certain embodiments, in the second period, the compound, or a pharmaceutically acceptable salt thereof, is administered at about 6 mg/day, about 8 mg/day, about 12 mg/day, about 16 mg per day, about 18 mg/day, about 20 mg/day, or about 24 mg per day. In certain embodiments, the maintenance dose (the amount per day administered during the second period) is about 33.3% of the amount per day administered during the first period. In certain embodiments, the maintenance dose is about 50% of the amount per day administered during the first period. In certain embodiments, the maintenance dose is about 66.7% of the amount per day administered during the first period. In certain embodiments, the maintenance dose is about 75% of the amount per day administered during the first period.

In certain embodiments, in the first period, the compound, or a pharmaceutically acceptable salt thereof, is administered at about 24 mg/day, and in the second period, the compound, or a pharmaceutically acceptable salt thereof, is administered at about 16 mg/day. In certain embodiments, the about 24 mg/day is administered in a single dose (i.e., once per day), and the about 16 mg/day is administered in a single dose (i.e., once per day). In certain embodiments, the about 24 mg/day is administered as two doses of about 12 mg each (i.e., about 12 mg twice per day), and the about 16 mg/day is administered as two doses of about 8 mg each (i.e., about 8 mg twice per day).

In certain embodiments, in the first period, the compound, or a pharmaceutically acceptable salt thereof, is administered at about 16 mg/day, and in the second period, the compound, or a pharmaceutically acceptable salt thereof, is administered at about 8 mg/day. In certain embodiments, the about 16 mg/day is administered in a single dose (i.e., once per day), and the about 8 mg/day is administered in a single dose (i.e., once per day). In certain embodiments, the about 16 mg/day is administered as two doses of about 8 mg each (i.e., about 8 mg twice per day), and the about 8 mg/day is administered as two doses of about 4 mg each (i.e., about 4 mg twice per day).

In certain embodiments, in the first period, the compound, or a pharmaceutically acceptable salt thereof, is administered at about 24 mg/day, and in the second period, the compound, or a pharmaceutically acceptable salt thereof, is administered at about 8 mg/day. In certain embodiments, the about 24 mg/day is administered in a single dose (i.e., once per day), and the about 8 mg/day is administered in a single dose (i.e., once per day). In certain embodiments, the about 24 mg/day is administered as two doses of about 12 mg each (i.e., about 12 mg twice per day), and the about 8 mg/day is administered as two doses of about 4 mg each (i.e., about 4 mg twice per day).

In certain embodiments, the compound, or a pharmaceutically acceptable salt thereof, is administered orally.

In certain embodiments, the compound, or a pharmaceutically acceptable salt thereof, is administered in a pharmaceutical formulation which is a tablet.

In certain embodiments, the compound, or a pharmaceutically acceptable salt thereof, is administered once per day (QD) in the first period. In certain embodiments, the compound, or a pharmaceutically acceptable salt thereof, is administered twice per day (BID) in the first period.

In certain embodiments, the compound, or a pharmaceutically acceptable salt thereof, is administered once per day (QD) in the second period. In certain embodiments, the compound, or a pharmaceutically acceptable salt thereof, is administered twice per day (BID) in the second period.

In certain embodiments, the first period is about 8-24 weeks. In certain embodiments, the first period is about 8 weeks. In certain embodiments, the first period is about 10 weeks. In certain embodiments, the first period is about 12 weeks. In certain embodiments, the first period is about 16 weeks. In certain embodiments, the first period is about 20 weeks. In certain embodiments, the first period is about 24 weeks.

In certain embodiments, the second period is at least 8 weeks. In certain embodiments, the second period is at least 12 weeks. In certain embodiments, the second period is at least 24 weeks.

In certain embodiments, in Compound (I), each position designated specifically as deuterium has at least 97% incorporation of deuterium.

In certain embodiments, the amount per day administered in the second period is about 50% of the amount per day administered in the first period. In certain embodiments, the amount per day administered in the second period is about 66.7% of the amount per day administered in the first period. In certain embodiments, the amount per day administered in the second period is about 75% of the amount per day administered in the first period.

It will be understood that reference to a specified amount of Compound (I), or a pharmaceutically acceptable salt thereof, includes both the stated amount of Compound (I) as the free base, and an amount of a pharmaceutically acceptable salt of Compound (I) (such as the phosphate salt) which is equivalent (in moles) to the stated amount of Compound (I) as the free base (e.g., 10.5 mg of Compound (I) phosphate salt is equivalent to 8 mg of Compound (I) free base).

In certain embodiments, the amount of Compound (I), or a pharmaceutically acceptable salt thereof (i.e., an equivalent amount of a pharmaceutically acceptable salt, such as the phosphate salt) administered in the method for treating hair loss disorders (e.g., in the first period or second period), is about 4 mg/day (such as 4 mg/day), about 8 mg/day (such as 8 mg/day), about 16 mg/day (such as 16 mg/day), about 24 mg/day (such as 24 mg/day), or about 32 mg/day (such as 32 mg/day).

In certain embodiments, the amount of Compound (I), or a pharmaceutically acceptable salt thereof (i.e., an equivalent amount of a pharmaceutically acceptable salt, such as the phosphate salt) administered in the method for treating hair loss disorders (e.g., in the first period or second period), is about 8 mg/day (such as 8 mg/day), about 16 mg/day (such as 16 mg/day), about 24 mg/day (such as 24 mg/day), or about 32 mg/day (such as 32 mg/day).

In certain embodiments, the amount of Compound (I), or a pharmaceutically acceptable salt thereof administered in the method for treating hair loss disorders (e.g., in the first period or second period), is about 8 mg/day (such as 8 mg/day), about 16 mg/day (such as 16 mg/day), about 24 mg/day (such as 24 mg/day), or about 32 mg/day (such as 32 mg/day). In certain embodiments, the amount of Compound (I), or a pharmaceutically acceptable salt thereof, is about 8 mg/day (such as 8 mg/day), about 12 mg/day (such as 12 mg/day), about 16 mg/day (such as 16 mg/day) or about 24 mg/day (such as 24 mg/day).

In certain embodiments, the amount of Compound (I), or a pharmaceutically acceptable salt thereof administered in the method for treating hair loss disorders (e.g., in the first period or second period), is about 8 mg/day (such as 8 mg/day), about 16 mg/day (such as 16 mg/day), about 24 mg/day (such as 24 mg/day), or about 32 mg/day (such as 32 mg/day). In certain embodiments, the amount of Compound (I), or a pharmaceutically acceptable salt thereof, is about 16 mg/day to about 32 mg/day, e.g., about 16 mg/day (such as 16 mg/day) about 24 mg/day (such as 24 mg/day), or about 32 mg/day (such as 32 mg/day).

In certain embodiments, the amount of Compound (I), or a pharmaceutically acceptable salt thereof administered in the method for treating hair loss disorders (e.g., in the first period or the second period), is 10.6 mg/day of Compound (I) phosphate, e.g., administered as a 10.6 mg dose once a day, or a 5.3 mg dose twice daily. In certain embodiments, the amount of Compound (I), or a pharmaceutically acceptable salt thereof, is 21.1 mg/day of Compound (I) phosphate, e.g., administered as a 21.1 mg dose once a day, or a 10.5 mg dose twice daily. In certain embodiments, the amount of Compound (I), or a pharmaceutically acceptable salt thereof, is 31.6 mg/day of Compound (I) phosphate, e.g., administered as a 31.6 mg dose once a day, or a 15.8 mg dose twice daily. In certain embodiments, the amount of Compound (I), or a pharmaceutically acceptable salt thereof, is 42.2 mg/day of Compound (I) phosphate, e.g., administered as a 42.2 mg dose once a day, or a 21.1 mg dose twice daily.

In certain embodiments, the amount of Compound (I), or a pharmaceutically acceptable salt thereof administered in the method for treating hair loss disorders (e.g., in the first period or the second period) is about 8 mg (such as 8 mg) twice per day. In a specific embodiment, Compound (I) is administered as about 10.5 mg (such as 10.5 mg) of the phosphate salt of Compound (I) twice per day.

In certain embodiments, the amount of Compound (I), or a pharmaceutically acceptable salt thereof, administered in the method for treating hair loss disorders (e.g., in the first period or the second period) is about 8 mg (such as 8 mg), e.g., as a single dose once a day, or twice per day in divided doses. In certain embodiments, the amount of Compound (I), or a pharmaceutically acceptable salt thereof administered in the method for treating hair loss disorders (e.g., in the first period or the second period) is about 12 mg (such as 12 mg) as a single dose once a day, or twice per day in divided doses. In a specific embodiment, Compound (I) is administered as about 15.8 mg (such as 15.8 mg) of the phosphate salt of Compound (I) as a single dose once a day, or twice per day in divided doses. In certain embodiments, the amount of Compound (I), or a pharmaceutically acceptable salt thereof administered in the method for treating hair loss disorders (e.g., in the first period or the second period) is about 16 mg (such as 16 mg) as a single dose once a day, or twice per day in divided doses. In a specific embodiment, Compound (I) is administered as about 21.1 mg (such as 21.1 mg) of the phosphate salt of Compound (I) as a single dose once a day, or twice per day in divided doses. In certain embodiments, the amount of Compound (I), or a pharmaceutically acceptable salt thereof administered in the method for treating hair loss disorders (e.g., in the first period or the second period) is about 24 mg (such as 24 mg) as a single dose once a day, or twice per day in divided doses. In certain embodiments, the amount of Compound (I), or a pharmaceutically acceptable salt thereof administered in the method for treating hair loss disorders (e.g., in the first period) is about 32 mg (such as 32 mg) once a day, or twice per day in divided doses.

In certain embodiments, the hair loss disorder is alopecia areata. In certain embodiments, the subject is a human. In one embodiment, the subject is a human 6 years of age or older. In certain embodiments, Compound (I), or a pharmaceutically acceptable salt thereof (such as the phosphate salt), is administered orally at any of the dosages described herein. In certain embodiments, the Compound (I), or a pharmaceutically acceptable salt thereof, is administered orally at any of the dosages described herein in a pharmaceutical formulation which is a tablet.

In certain embodiments, the amount of Compound (I), or a pharmaceutically acceptable salt thereof, that is administered in the second period is an amount per day that is about 50 percent of the amount per day administered during the first period. In certain embodiments, the amount of Compound (I), or a pharmaceutically acceptable salt thereof, that is administered in the second period is an amount per day that is about 66.7 percent of the amount per day administered during the first period. In certain embodiments, the amount of Compound (I), or a pharmaceutically acceptable salt thereof, that is administered in the second period is an amount per day that is about 75% percent of the amount per day administered during the first period.

Exemplary amounts of Compound (I) or a pharmaceutically acceptable salt thereof, to be administered are shown in the Table below:

| First Period | Second Period |
|---|---|
| 8 mg/day | 6 mg/day |
| 8 mg/day | 4 mg/day |
| 12 mg/day | 8 mg/day |
| 12 mg/day | 6 mg/day |
| 16 mg/day | 12 mg/day |
| 16 mg/day | 8 mg/day |
| 24 mg/day | 16 mg/day |
| 24 mg/day | 18 mg/day |
| 24 mg/day | 12 mg/day |
| 32 mg/day | 24 mg/day |
| 32 mg/day | 16 mg/day |

In another aspect, the invention provides a method of treating alopecia areata in a human subject in need thereof, the method comprising:

a) administering to the human subject over a first period an initial dose of a compound represented by the following structural formula:

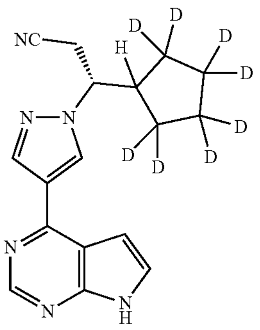 [SMILES: [2H]C1([2H])C([C@@H](CC#N)n2cc(-c3ncnc4[nH]ccc34)cn2)C([2H])([2H])C([2H])([2H])C1([2H])[2H]]

or a pharmaceutically acceptable salt thereof, wherein each position designated specifically as deuterium has at least 95% incorporation of deuterium, wherein the length of the first period is sufficient to achieve a reduction in the SALT score of the patient, and wherein the initial dose is from about 8 to about 32 mg per day, followed by;

b) administering a maintenance dose of the compound or a pharmaceutically acceptable salt thereof to the human subject over a second period, wherein the maintenance dose is from 50% to 75% of the initial dose and, wherein the maintenance dose is sufficient to maintain hair growth (e.g., a SALT score of less than or equal to 20).

In certain embodiments, the length of the first period is sufficient to achieve a reduction in the SALT score of the patient of at least 10% relative to baseline (for example, from a SALT score of 100 prior to treatment to a SALT score of 90 after treatment) In further embodiments, the length of the first period is sufficient to achieve a reduction in the SALT score of the patient of at least 20%, at least 30%, at least 40%, at least 50%, at least 60%, at least 70%, at least 75%, at least 80%, or at least 90% relative to baseline. In certain embodiments, the length of the first period is sufficient to achieve a reduction in the SALT score of the patient of at least 50% relative to baseline. In certain embodiments, the length of the first period is sufficient to achieve a reduction in the SALT score of the patient of at least 75% relative to baseline. In certain embodiments, the length of the first period is sufficient to achieve a reduction in the SALT score of the patient of at least 90% relative to baseline.

In certain embodiments, the length of the first period is sufficient to achieve a SALT score at the end of the first period of less than or equal to 50, less than or equal to 40, less than or equal to 30, less than or equal to 20, less than or equal to 15, less than or equal to 10, less than or equal to 5, less than or equal to 1, or zero. In certain embodiments, the length of the first period is sufficient to achieve a SALT score at the end of the first period of less than or equal to 20. In certain embodiments, the length of the first period is sufficient to achieve a SALT score at the end of the first period of less than or equal to 15. In certain embodiments, the length of the first period is sufficient to achieve a SALT score at the end of the first period of less than or equal to 10. In certain embodiments, the length of the first period is sufficient to achieve a SALT score at the end of the first period of less than or equal to 5. In certain embodiments, the length of the first period is sufficient to achieve a SALT score at the end of the first period of less than or equal to 1. In certain embodiments, the length of the first period is sufficient to achieve a SALT score at the end of the first period of zero.

In certain embodiments, the maintenance dose is about 25% of the initial dose. In certain embodiments, the maintenance dose is about 33.3% of the initial dose. In certain embodiments, the maintenance dose is about 50% of the initial dose. In certain embodiments, the maintenance dose is about 66.7% of the initial dose. In certain embodiments, the maintenance dose is about 75% of the initial dose.

In certain embodiments, the maintenance dose given during the second period is sufficient to achieve a SALT score at the end of the second period of less than or equal to 50, less than or equal to 40, less than or equal to 30, less than or equal to 20, less than or equal to 15, less than or equal to 10, less than or equal to 5, less than or equal to 1, or zero. In certain embodiments, the maintenance dose given during the second period is sufficient to achieve a SALT score at the end of the second period of less than or equal to 20. In certain embodiments, the maintenance dose given during the second period is sufficient to achieve a SALT score at the end of the second period of less than or equal to 15. In certain embodiments, the maintenance dose given during the second period is sufficient to achieve a SALT score at the end of the second period of less than or equal to 10. In certain embodiments, the maintenance dose given during the second period is sufficient to achieve a SALT score at the end of the second period of less than or equal to 5. In certain embodiments, the maintenance dose is sufficient maintain the SALT score achieved in the first period (e.g. In certain embodiments, the maintenance dose given during the second period is sufficient to achieve a <10-point or <5-point increase in the subject's SALT score at the end of the second period relative to the subject's SALT score at the end of the first period. In certain embodiments, the maintenance dose given during the second period is sufficient to achieve a <30% increase in the subject's SALT score at the end of the second period relative to the subject's SALT score at the end of the first period. In certain embodiments, the maintenance dose given during the second period is sufficient to achieve a <5-point increase and <30% increase in the subject's SALT score at the end of the second period relative to the subject's SALT score at the end of the first period. In certain embodiments, the maintenance dose is sufficient to achieve a <4-point increase, a <3-point increase, a <2-point increase, or a <1-point increase in the subject's SALT score at the end of the second period relative to the subject's SALT score at the end of the first period. In certain embodiments, the maintenance dose is sufficient to achieve a <20% increase, a <15% increase, a <10% increase, or a <5% increase in the subject's SALT score at the end of the second period relative to the subject's SALT score at the end of the first period.

In another aspect, the invention provides a method of treating a hair loss disorder in a human subject, the method comprising administering to the subject a compound represented by the following structural formula:

Compound (I)

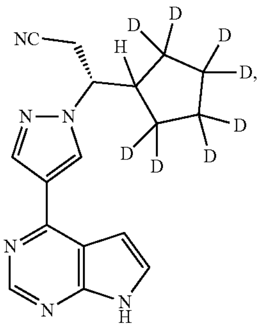

wherein each position specifically designated as deuterium has at least 95% incorporation of deuterium; or a pharmaceutically acceptable salt thereof; wherein the compound, or pharmaceutically acceptable salt thereof, is first administered for an induction period to initiate hair growth and then administered for a second period to further treat the hair disorder, wherein the induction period is at least 8 weeks and no greater than 24 weeks, the amount of compound, or pharmaceutically acceptable salt thereof, administered during the induction period is in the range of 16 mg per day and 32 mg per day, and following the induction period the amount of compound, or pharmaceutically acceptable salt thereof, administered is reduced by 50 to 75 percent (e.g., 50, 66.7 or 75%) for the second period.

In the above aspects:

In certain embodiments, the first period is from 8 to 24 weeks in length. In certain embodiments, the first period is about 12 weeks. In certain embodiments, the first period is about 16 weeks. In certain embodiments, the first period is about 20 weeks. In certain embodiments, the first period is about 24 weeks.

In certain embodiments, the second period is at least 12 weeks in length. In certain embodiments, the second period is at least 24 weeks.

Exemplary doses for the first and second periods are described above.

In certain embodiments, wherein the reduction in the baseline SALT score of the patient in the first period is from about 10% to about 50%. In certain embodiments, the reduction in the baseline SALT score is from about 20% to about 50%. In certain embodiments, the reduction in the baseline SALT score of the patient in the first period is about 50%. In certain embodiments, the reduction in the baseline SALT score is from about 30% to about 50%. In certain embodiments, the reduction in the baseline SALT score of the patient in the first period is at least 50%. In certain embodiments, the reduction in the baseline SALT score is from about 50% to about 99%. In certain embodiments, the reduction in the baseline SALT score is from about 50% to about 90%. In certain embodiments, the reduction in the baseline SALT score is from about 50% to about 75%. In certain embodiments, the reduction in the baseline SALT score is from about 75% to about 90%.

In certain embodiments, in the first period, the compound, or a pharmaceutically acceptable salt thereof, is administered at about 12 mg/day, about 16 mg/day, about 24 mg/day, or about 32 mg per day.

In certain embodiments, in the second period, the compound, or a pharmaceutically acceptable salt thereof, is administered at about 6 mg/day, about 8 mg/day, about 12 mg/day, or about 16 mg per day.

In certain embodiments in the first period, the compound, or a pharmaceutically acceptable salt thereof, is administered at about 24 mg/day, and in the second period, the compound, or a pharmaceutically acceptable salt thereof, is administered at about 16 mg/day. In certain embodiments, the about 24 mg/day is administered once per day, and the about 16 mg/day is administered once per day. In certain embodiments, the about 24 mg/day is administered as about 12 mg twice per day (divided doses), and the about 16 mg/day is administered as about 8 mg twice per day (divided doses).

In certain embodiments, in the first period, the compound, or a pharmaceutically acceptable salt thereof, is administered at about 16 mg/day, and in the second period, the compound, or a pharmaceutically acceptable salt thereof, is administered at about 8 mg/day.

In certain embodiments, the compound, or a pharmaceutically acceptable salt thereof, is administered orally.

In certain embodiments, the compound, or a pharmaceutically acceptable salt thereof, is administered in a pharmaceutical formulation which is a tablet. In certain embodiments, the compound, or a pharmaceutically acceptable salt thereof, is administered in a pharmaceutical formulation which is a capsule.

In certain embodiments, the compound, or a pharmaceutically acceptable salt thereof, is administered once per day in the first period.

In certain embodiments, the compound, or a pharmaceutically acceptable salt thereof, is administered twice per day in the first period.

In certain embodiments in Compound (I), each position designated specifically as deuterium has at least 97% incorporation of deuterium.

In the methods of the invention, the first and second periods can vary in length according to factors such as the amount of hair growth induced in the first period (e.g., as determined by SALT score measured before and after the first period), and the duration of treatment desired. The first period can be, e.g., 8-24 weeks, e.g., 8 weeks, 10 weeks, 12 weeks, 14 weeks, 16 weeks, 18 weeks, 20 weeks, 22 weeks, or 24 weeks. The second period can be, e.g., 8 weeks, 16 weeks, 24 weeks, 52 weeks, 2 years, 5 years, 10 years, or 20 years.

In one embodiment, the first period at least 24 weeks (e.g., 24 weeks) and the second period is at least 24 weeks (e.g., 24 weeks).

In another embodiment, the first period is up to 24 weeks and the second period is at least 24 weeks (e.g., 24 weeks).

In another aspect, the invention provides a method for inducing hair growth in a subject. The method comprises administering to a mammalian subject an effective amount of Compound (I), or a pharmaceutically acceptable salt thereof (i.e., an equivalent amount of a pharmaceutically acceptable salt, such as the phosphate salt), wherein each position designated specifically as deuterium has at least 95% incorporation of deuterium; or a pharmaceutically acceptable salt thereof; wherein the compound, or pharmaceutically acceptable salt thereof, is administered for (1) a first period of 8-24 weeks in an amount in the range of 8 mg to 32 mg per day, followed by (2) a second period of at least 8 weeks wherein the compound, or pharmaceutically acceptable salt thereof, is administered in an amount per day that is 50 to 75 percent (e.g., 50%, 66.7%, 75%) of the amount per day administered during the first period, such that hair growth is induced in the subject.

In certain embodiments, the amount of Compound (I), or a pharmaceutically acceptable salt thereof administered in the method for inducing hair growth, is about 4 mg/day (such as 4 mg/day), about 8 mg/day (such as 8 mg/day), about 16 mg/day (such as 16 mg/day), about 24 mg/day (such as 24 mg/day), about 32 mg/day (such as 32 mg/day) or about 48 mg/day (such as 48 mg/day).

In certain embodiments, the amount of Compound (I), or a pharmaceutically acceptable salt thereof administered in the method for inducing hair growth, is about 16 mg/day (such as 16 mg/day), about 24 mg/day (such as 24 mg/day) or about 32 mg/day (such as 32 mg/day).

In certain embodiments, the amount of Compound (I), or a pharmaceutically acceptable salt thereof administered in the method for inducing hair growth, is about 8 mg/day (such as 8 mg/day), about 16 mg/day (such as 16 mg/day), about 24 mg/day (such as 24 mg/day), or about 32 mg/day (such as 32 mg/day). In certain embodiments, the amount of Compound (I), or a pharmaceutically acceptable salt thereof administered in the method for inducing hair growth, is about 8 mg/day (such as 8 mg/day), about 12 mg/day (such as 12/mg/day), about 16 mg/day (such as 16 mg/day), or about 24 mg/day (such as 24 mg/day).

In certain embodiments, the amount of Compound (I), or a pharmaceutically acceptable salt thereof administered in the method for inducing hair growth, is 10.6 mg/day of Compound (I) phosphate, e.g., administered as a 10.6 mg dose once a day or a 5.3 mg dose twice daily. In certain embodiments, the amount of Compound (I), or a pharmaceutically acceptable salt thereof, is 21.1 mg/day of Compound (I) phosphate, e.g., administered as a 21.1 mg dose once a day or a 10.5 mg dose twice daily. In certain embodiments, the amount of Compound (I), or a pharmaceutically acceptable salt thereof, is 31.6 mg/day of Compound (I) phosphate, e.g., administered as a 31.6 mg dose once a day or a 15.8 mg dose twice daily. In certain embodiments, the amount of Compound (I), or a pharmaceutically acceptable salt thereof, is 42.2 mg/day of Compound (I) phosphate, e.g., administered as a 42.2 mg dose once a day or a 21.1 mg dose twice daily.

In certain embodiments, the amount of Compound (I), or a pharmaceutically acceptable salt thereof administered in the method for inducing hair growth (e.g., in the second period) is about 4 mg (such as 4 mg) twice per day. In a specific embodiment, Compound (I) is administered as about 5.3 mg (such as 5.3 mg) of the phosphate salt of Compound (I) twice per day.

In certain embodiments, the amount of Compound (I), or a pharmaceutically acceptable salt thereof administered in the method for inducing hair growth (e.g., in the first or second period) is about 8 mg (such as 8 mg) twice per day. In a specific embodiment, Compound (I) is administered as about 10.5 mg (such as 10.5 mg) of the phosphate salt of Compound (I) twice per day.

In certain embodiments, the amount of Compound (I), or a pharmaceutically acceptable salt thereof administered in the method for inducing hair growth (e.g., in the first or second period) is about 12 mg (such as 12 mg) twice per day. In a specific embodiment, Compound (I) is administered as the about 15.8 mg (such as 15.8 mg) of the phosphate salt of Compound (I) twice per day.

In certain embodiments, the amount of Compound (I), or a pharmaceutically acceptable salt thereof administered in the method for inducing hair growth (e.g., in the first period) is about 16 mg (such as 16 mg) twice per day. In a specific embodiment, Compound (I) is administered as the about 21.1 mg (such as 21.1 mg) of the phosphate salt of Compound (I) twice per day.

In certain embodiments, the subject suffers from a hair loss disorder; in further embodiments, the hair loss disorder is alopecia areata. In certain embodiments, the subject is a human. In one embodiment, the subject is a human 6 years of age or older. Preferably, Compound (I), or a pharmaceutically acceptable salt thereof (such as the phosphate salt), is administered orally at any of the foregoing dosages. Preferably, the Compound (I), or a pharmaceutically acceptable salt thereof, is administered orally at any of the foregoing dosages in a pharmaceutical formulation which is a tablet or capsule.

Hair loss disorders include, without limitation, androgenetic alopecia, alopecia areata, telogen effluvium, alopecia totalis, and alopecia universalis.

In a specific embodiment of any of the methods described herein, the condition is alopecia areata in a subject such as a mammalian (e.g., human) patient in need thereof. In certain embodiments, the alopecia areata is moderate to severe alopecia areata (for example, hair loss over at least 30% of the scalp, hair loss over at least 40% of the scalp, hair loss over at least 50% of the scalp, or hair loss over at least 75% of the scalp).

In one embodiment of any aspect, the compound is administered orally once a day. In other embodiments of any aspect, the compound is administered orally twice per day.

Effective doses will also vary, as recognized by those skilled in the art, depending on the diseases treated, the severity of the disease, the route of administration, the sex, age and general health condition of the subject, excipient usage, the possibility of co-usage with other therapeutic treatments such as use of other agents and the judgment of the treating physician.

The administration of Compound (I), or a pharmaceutically acceptable salt thereof (such as the phosphate salt), can continue for as long as necessary to treat a hair loss disorder, e.g., for one week, two weeks, one month, two months, three months, four months, six months, one year, two years, five years, ten years, or longer.

In certain embodiments, treatment is continued for a period of at least 8 weeks, or at least 12 weeks, or at least 16 weeks, or at least 20 weeks, or at least 24 weeks, or at least 28 weeks, or at least 32 weeks, or at least 36 weeks, or at least 40 weeks, or at least 44 weeks, or at least 48 weeks, or at least 52 weeks.

In certain embodiments, Compound (I), or a pharmaceutically acceptable salt thereof, is administered in combination with an additional therapeutic agent. Preferably, the additional therapeutic agent is an agent useful in the treatment of hair loss disorders or autoimmune conditions, such as inhibitors of JAK1, JAK2, or JAK3, and/or STAT1. Such inhibitors include ruxolitinib, tofacitinib, baricitinib, filgotinib, and the like. Other orally administered additional therapeutic agents include agents used in the treatment of alopecia areata, including, for example, oral corticosteroids.

For pharmaceutical compositions that comprise an additional therapeutic agent, an effective amount of the additional therapeutic agent is between about 20% and 100% of the dosage normally utilized in a monotherapy regime using just that agent. Preferably, an effective amount is between about 70% and 100% of the normal monotherapeutic dose.

The normal monotherapeutic dosages of these additional therapeutic agents are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif (2000); the FDA-approved labeling information for ruxolitinib and tofacitinib; and clinical trial information for baricitinib and filgotinib, each of which references are incorporated herein by reference in their entirety.

Some of the additional therapeutic agents referenced above may act synergistically with the compounds of this invention. When this occurs, it will allow the effective dosage of the additional therapeutic agent and/or Compound (I), or a pharmaceutically acceptable salt thereof, to be reduced from that required in a monotherapy. This has the advantage of minimizing toxic side effects of either the additional therapeutic agent or Compound (I), or a pharmaceutically acceptable salt thereof, synergistic improvements in efficacy, improved ease of administration or use and/or reduced overall expense of compound preparation or formulation.

In another embodiment, any of the above methods of treatment comprises the further step of co-administering to the subject in need thereof one or more additional therapeutic agents. The choice of additional therapeutic agent may be made from any additional therapeutic agent known to be useful for treatment of hair loss disorders such as alopecia areata. The choice of additional therapeutic agent is also dependent upon the particular disease or condition to be treated. Examples of additional therapeutic agents that may be employed in the methods of this invention are those set forth above for use in combination compositions comprising Compound (I), or a pharmaceutically acceptable salt thereof, and an additional therapeutic agent. Additional therapeutic agents include agents used in the treatment of alopecia areata, including, for example, topical minoxidil, injected corticosteroids, and anthralin cream or ointment.

The term "co-administered" as used herein means that the additional therapeutic agent may be administered together with Compound (I) or a pharmaceutically acceptable salt thereof, as part of a single dosage form (such as a composition of this invention comprising a compound of the invention and a second therapeutic agent as described above) or as separate, multiple dosage forms. Alternatively, the additional agent may be administered prior to, consecutively with, or following the administration of Compound (I), or a pharmaceutically acceptable salt thereof. In such combination therapy treatment, both Compound (I), or a pharmaceutically acceptable salt thereof, and the additional therapeutic agent(s) are administered by conventional methods. The administration of a composition of this invention, comprising both Compound (I), or a pharmaceutically acceptable salt thereof, and an additional therapeutic agent, to a subject does not preclude the separate administration of that same therapeutic agent, any other additional therapeutic agent or Compound (I), or a pharmaceutically acceptable salt thereof, to said subject at another time during a course of treatment.

Effective amounts of these additional therapeutic agents are well known to those skilled in the art and guidance for dosing may be found in patents and published patent applications referenced herein, as well as in Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), and other medical texts. However, it is well within the skilled artisan's purview to determine the additional therapeutic agent's optimal effective-amount range.

In one embodiment of the invention, where an additional therapeutic agent is administered to a subject, the effective amount of Compound (I), or a pharmaceutically acceptable salt thereof, is less than its effective amount would be where the additional therapeutic agent is not administered. In another embodiment, the effective amount of the additional therapeutic agent is less than its effective amount would be where Compound (I), or a pharmaceutically acceptable salt thereof, is not administered. In this way, undesired side effects associated with high doses of either agent may be minimized. Other potential advantages (including without limitation improved dosing regimens and/or reduced drug cost) will be apparent to those of skill in the art.

In yet another aspect, the invention provides the use of Compound (I), or a pharmaceutically acceptable salt thereof (i.e., an equivalent amount of a pharmaceutically acceptable salt, such as the phosphate salt), alone or together with one or more of the above-described additional therapeutic agents in the manufacture of a medicament, either as a single composition or as separate dosage forms, for treatment or prevention in a subject of a disease, disorder or symptom set forth above. Another aspect of the invention is Compound (I), or a pharmaceutically acceptable salt thereof, for use in the treatment or prevention in a subject of a disease, disorder or symptom thereof delineated herein.

Another aspect of the invention is a pharmaceutical composition comprising Compound (I), in the range of about 4 mg to about 50 mg (for example, about 5 mg, about 10 mg, about 20 mg, about 30 mg, about 40 mg, or about 50 mg), or an equivalent amount of a pharmaceutically acceptable salt thereof, together with a pharmaceutically acceptable carrier or diluent. In certain embodiments, the amount of Compound (I), or a pharmaceutically acceptable salt thereof, is about 4 mg, 8 mg, 16 mg, 24 mg, 32 mg or 48 mg. In certain embodiments, the amount of Compound (I), or a pharmaceutically acceptable salt thereof, is 4 mg, 8 mg, 12 mg, or 16 mg. In certain embodiments, the amount of Compound (I), or a pharmaceutically acceptable salt thereof, is 5.3 mg of Compound (I) phosphate. In certain embodiments, the amount of Compound (I), or a pharmaceutically acceptable salt thereof, is 10.5 or 10.6 mg of Compound (I) phosphate. In certain embodiments, the amount of Compound (I), or a pharmaceutically acceptable salt thereof, is 15.8 mg of Compound (I) phosphate. In certain embodiments, the amount of Compound (I), or a pharmaceutically acceptable salt thereof, is 21.1 mg of Compound (I) phosphate. In certain embodiments, the pharmaceutical composition is a tablet or capsule.

Another aspect of the invention is a unit dose form comprising Compound (I), in the range of about 4 mg to about 50 mg (for example, about 5 mg, about 10 mg, about 20 mg, about 30 mg, about 40 mg, or about 50 mg), or an equivalent amount of a pharmaceutically acceptable salt thereof, together with a pharmaceutically acceptable carrier or diluent. In certain embodiments, the amount of Compound (I), or a pharmaceutically acceptable salt thereof, is about 4 mg, 8 mg, 16 mg, 24 mg, 32 mg or 48 mg. In certain embodiments, the amount of Compound (I), or a pharmaceutically acceptable salt thereof, is 4 mg, 8 mg, 12 mg, or 16 mg. In certain embodiments, the amount of Compound (I), or a pharmaceutically acceptable salt thereof, is 5.3 mg of Compound (I) phosphate. In certain embodiments, the amount of Compound (I), or a pharmaceutically acceptable salt thereof, is 10.5 or 10.6 mg of Compound (I) phosphate.

In certain embodiments, the amount of Compound (I), or a pharmaceutically acceptable salt thereof, is 15.8 mg of Compound (I) phosphate. In certain embodiments, the amount of Compound (I), or a pharmaceutically acceptable salt thereof, is 21.1 mg of Compound (I) phosphate. In certain embodiments, the unit dose form is a tablet or capsule.

In one embodiment, any atom not designated as deuterium is present at its natural isotopic abundance in Compound (I), or a pharmaceutically acceptable salt thereof.

The synthesis of Compound (I), or a pharmaceutically acceptable salt thereof (such as the phosphate salt) may be readily achieved by the methods described U.S. Pat. No. 9,249,149, PCT Patent Publication WO2017/192905, or PCT Patent Publication WO2020/163653, the teachings of which are incorporated herein by reference, with appropriate modifications. For example, U.S. Pat. No. 9,249,149 describes the use of a D9-intermediate 15 to produce a D9-ruxolitinib product; use of the intermediate A

A

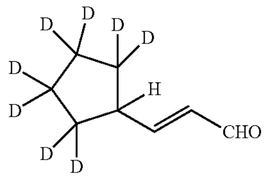

in the methods described in U.S. Pat. No. 9,249,149 furnishes Compound (I). Additionally, intermediate B

B

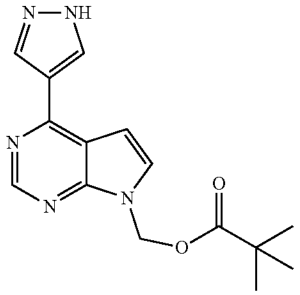

can be used instead of intermediate 14 of U.S. Pat. No. 9,249,149 to prepare Compound (I); removal of the amino protecting group can be accomplished with basic cleavage (e.g., with sodium hydroxide). Phosphoric acid can be used to convert Compound (I) (Free base) to its phosphate salt. Additional methods of preparing ruxolitinib (i.e., non-deuterated Compound (I)) are disclosed in U.S. Pat. No. 9,000, 161, and can be used, with use of suitable deuterated reagents, to prepare Compound (I).

Such methods can be carried out utilizing corresponding deuterated and optionally, other isotope-containing reagents and/or intermediates to synthesize the compounds delineated herein, or invoking standard synthetic protocols known in the art for introducing isotopic atoms to a chemical structure.

The invention also provides pharmaceutical compositions comprising an effective amount of Compound (I), or a pharmaceutically acceptable salt thereof (i.e., an equivalent amount of a pharmaceutically acceptable salt, such as the phosphate salt); and a pharmaceutically acceptable carrier. The carrier(s) are "acceptable" in the sense of being compatible with the other ingredients of the formulation and, in the case of a pharmaceutically acceptable carrier, not deleterious to the recipient thereof in an amount used in the medicament. In certain embodiments, the pharmaceutical composition is provided as a unit dose form.

The invention provides a pharmaceutical composition comprising a pharmaceutically acceptable carrier or diluent and 4 to 50 mg of a compound represented by the following structural formula:

Compound (I)

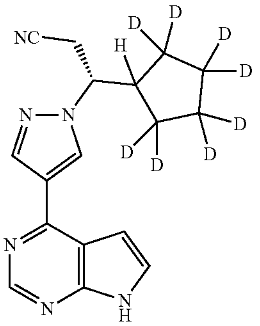

or a pharmaceutically acceptable salt thereof (i.e., an equivalent amount of a pharmaceutically acceptable salt, such as the phosphate salt). For example, the amount of Compound (I) is 4 mg, 8 mg, 12 mg, 16 mg or 24 mg.

Pharmaceutically acceptable carriers, adjuvants and vehicles that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

If required, the solubility and bioavailability of the compounds of the present invention in pharmaceutical compositions may be enhanced by methods well-known in the art. One method includes the use of lipid excipients in the formulation. See "Oral Lipid-Based Formulations: Enhancing the Bioavailability of Poorly Water-Soluble Drugs (Drugs and the Pharmaceutical Sciences)," David J. Hauss, ed. Informa Healthcare, 2007; and "Role of Lipid Excipients in Modifying Oral and Parenteral Drug Delivery: Basic Principles and Biological Examples," Kishor M. Wasan, ed. Wiley-Interscience, 2006.

Another known method of enhancing bioavailability is the use of an amorphous form of a compound of this invention optionally formulated with a poloxamer, such as LUTROL™ and PLURONIC™ (BASF Corporation), or block copolymers of ethylene oxide and propylene oxide. See U.S. Pat. No. 7,014,866; and United States patent publications 20060094744 and 20060079502.

The pharmaceutical compositions of the invention include those suitable for oral administration. Other formulations may conveniently be presented in unit dosage form, e.g., tablets, sustained release capsules, granules, and in liposomes, and may be prepared by any methods well known in the art of pharmacy. See, for example, Remington: The Science and Practice of Pharmacy, Lippincott Williams & Wilkins, Baltimore, MD (20th ed. 2000).

Such preparative methods include the step of bringing into association with the molecule to be administered ingredients such as the carrier that constitutes one or more accessory ingredients. In general, the compositions are prepared by uniformly and intimately bringing into association the active ingredients with liquid carriers, liposomes or finely divided solid carriers, or both, and then, if necessary, shaping the product.

In certain embodiments, the compound is administered orally. Compositions of the present invention suitable for oral administration may be presented as discrete units such as capsules, sachets, or tablets each containing a predetermined amount of the active ingredient; a powder or granules; a solution or a suspension in an aqueous liquid or a non-aqueous liquid; an oil-in-water liquid emulsion; a water-in-oil liquid emulsion; packed in liposomes; or as a bolus, etc. Soft gelatin capsules can be useful for containing such suspensions, which may beneficially increase the rate of compound absorption. In a specific embodiment, the compound is administered orally as a tablet. In another specific embodiment, the compound is administered orally in a capsule.

In the case of tablets for oral use, carriers that are commonly used include lactose and corn starch. Lubricating agents, such as magnesium stearate, are also typically added. For oral administration in a capsule form, useful diluents include lactose and dried cornstarch. When aqueous suspensions are administered orally, the active ingredient is combined with emulsifying and suspending agents. If desired, certain sweetening and/or flavoring and/or coloring agents may be added. In another embodiment, the composition is in the form of a tablet. In certain embodiments, exemplary formulations for the tablet are disclosed in U.S. Pat. No. 8,754,224, the teachings of which are herein incorporated by reference.

In a particular embodiment, a tablet formulation contains about 4 mg to about 50 mg of Compound (I), or an equivalent amount of a pharmaceutically acceptable salt thereof (such as the phosphate salt), and the following inactive ingredients: colloidal silicon dioxide, magnesium stearate, microcrystalline cellulose, and povidone. Wet granulation followed by compression provides tablets comprising Compound (I), or a pharmaceutically acceptable salt thereof. For example, to prepare a 200 mg tablet comprising the equivalent of 16 mg of Compound (I), 10.6 wt % of Compound (I) phosphate and 64.44 wt % Avicel PH-101 microcrystalline cellulose are mixed in a higher shear granulator, and an 8.5% w/w aqueous Kollidon 30 solution (containing Kollidon 30, a polyvinylpyrrolidone (povidone); 5 wt % (based on the total formulation weight) is added during mixing to form granules. The granules are tray-dried in an oven at 60±10° C. and milled using a Quadro Comil U5 mill. The granules retained on the comil screen are forced through a #20 mesh sieve using a stainless steel spatula. The resulting milled granules are mixed with Avicel PH-200 microcrystalline cellulose (18.5 wt %), Aerosil 200 colloidal silicon dioxide (0.5 wt %) and Hyqual magnesium stearate (1 wt %) in a Turbula mixer to form the final blend. The final blend is compressed into 200 mg tablets using a Riva Piccola rotary press tooled with 0.451"×0.229" D-type modified capsule shape tooling. Each tablet contains 21.1 mg Compound (I) (equivalent to 16 mg of Compound (I) free base).

In a particular embodiment, the tablet contains about 10.5 mg or about 10.6 mg of the phosphate salt of Compound (I) (equivalent to 8 mg of Compound (I) free base).

In a particular embodiment, the tablet comprises the following ingredients:

| 4 mg Tablet | | | |
|---|---|---|---|
| Component | Function | Wt % | Amount per unit (mg) |
| Compound (I) Phosphate | Active | 2.6 | 5.3* |
| Microcrystalline Cellulose | Diluent/Binder | 90.9 | 181.7 |
| Povidone | Binder | 5.0 | 10.0 |
| Colloidal Silicon Dioxide | Glidant | 0.5 | 1.0 |
| Magnesium Stearate | Lubricant | 1.0 | 2.0 |
| Purified Water | Solvent | Removed during processing | |
| | Total | 100.0 | 200.0 |

*Equivalent to 4 mg Compound (I) free base

In another particular embodiment, the tablet comprises the following ingredients:

| 8 mg Tablet | | | |
|---|---|---|---|
| Component | Function | Wt % | Amount per unit (mg) |
| Compound (I) Phosphate | Active | 5.2 | 10.5* |
| Microcrystalline Cellulose | Diluent/Binder | 90.8 | 181.5 |
| Povidone | Binder | 2.5 | 5.0 |
| Colloidal Silicon Dioxide | Glidant | 0.5 | 1.0 |
| Magnesium Stearate | Lubricant | 1.0 | 2.0 |
| Purified Water | Solvent | Removed during processing | |
| | Total | 100.0 | 200.0 |

*Equivalent to 8 mg Compound (I) free base

In an alternative particular embodiment, the tablet comprises the following ingredients:

| 8 mg Tablet | | | |
|---|---|---|---|
| Component | Function | Wt % | Amount per unit (mg) |
| Compound (I) Phosphate | Active | 5.3 | 10.6* |
| Microcrystalline Cellulose | Diluent/Binder | 88.2 | 176.4 |
| Povidone | Binder | 5.0 | 10.0 |
| Colloidal Silicon Dioxide | Glidant | 0.5 | 1.0 |
| Magnesium Stearate | Lubricant | 1.0 | 2.0 |
| Purified Water | Solvent | Removed during processing | |
| | Total | 100.0 | 200.0 |

*Equivalent to 8 mg Compound (I) free base

In still another particular embodiment, the tablet comprises the following ingredients:

| 16 mg Tablet | | | |
|---|---|---|---|
| Component | Function | Wt % | Amount per unit (mg) |
| Compound (I) Phosphate | Active | 10.6 | 21.1* |
| Microcrystalline Cellulose | Diluent/Binder | 82.9 | 165.9 |
| Povidone | Binder | 5.0 | 10.0 |

-continued

| 16 mg Tablet | | | |
|---|---|---|---|
| Component | Function | Wt % | Amount per unit (mg) |
| Colloidal Silicon Dioxide | Glidant | 0.5 | 1.0 |
| Magnesium Stearate | Lubricant | 1.0 | 2.0 |
| Purified Water | Solvent | Removed during processing | |
| | Total | 100.0 | 200.0 |

*Equivalent to 16 mg Compound (I) free base

In another embodiment, a composition of this invention further comprises an additional therapeutic agent. The additional therapeutic agent may be selected from any compound or therapeutic agent known to have or that demonstrates advantageous properties when administered with a compound having the same mechanism of action as ruxolitinib.

Preferably, the additional therapeutic agent is an agent useful in the treatment of hair loss disorders or autoimmune conditions, including inhibitors of JAK1, JAK2, or JAK3, and/or STAT1. Such inhibitors include ruxolitinib, tofacitinib, baricitinib, filgotinib, and the like. Other additional therapeutic agents include oral corticosteroids.

In another embodiment, the invention provides separate dosage forms of Compound (I), or a pharmaceutically acceptable salt thereof, and one or more of any of the above-described additional therapeutic agents, wherein Compound (I), or a pharmaceutically acceptable salt thereof, and additional therapeutic agent are associated with one another. The term "associated with one another" as used herein means that the separate dosage forms are packaged together or otherwise attached to one another such that it is readily apparent that the separate dosage forms are intended to be sold and administered together (within less than 24 hours of one another, consecutively or simultaneously).

In the pharmaceutical compositions of the invention, Compound (I), or a pharmaceutically acceptable salt thereof, is present in an effective amount. As used herein, the term "effective amount" refers to an amount which, when administered in a proper dosing regimen, is sufficient to treat the target disorder.

The interrelationship of dosages for animals and humans (based on milligrams per meter squared of body surface) is described in Freireich et al., Cancer Chemother. Rep, 1966, 50: 219. Body surface area may be approximately determined from height and weight of the subject. See, e.g., Scientific Tables, Geigy Pharmaceuticals, Ardsley, N.Y., 1970, 537.

In one embodiment, an effective amount of Compound (I) (either as the free base, or as an equivalent amount of a pharmaceutically acceptable salt, such as the phosphate salt) can range from about 8 mg to 32 mg per day (such as 8 mg to 32 mg per day), such as, about 10 mg/day (such as 10 mg/day), about 20 mg/day (such as 20 mg/day), or about 30 mg/day (such as 30 mg/day). In certain embodiments, the amount is about 8 mg/day (such as 8 mg/day), about 12 mg/day (such as 12 mg/day), about 16 mg/day (such as 16 mg/day), about 24 mg/day (such as 24 mg/day), or about 32 mg/day (such as 32 mg/day). In one embodiment, a dose of about 8 mg/day (such as 8 mg/day), about 16 mg/day (such as 16 mg/day), about 24 mg/day (such as 24 mg/day), or about 32 mg/day (such as 32 mg/day) is administered once a day. In a specific example, a dose of 16 mg/day is administered as two 8 mg tablets of Compound (I) (either as the free base, or as an equivalent amount of a pharmaceutically acceptable salt, such as the phosphate salt) administered together (i.e., as a single dose). In another specific example, a dose of 16 mg/day is administered as one 16 mg tablet of Compound (I) (either as the free base, or as an equivalent amount of a pharmaceutically acceptable salt, such as the phosphate salt). In another embodiment, a dose of 8 mg/day, 16 mg/day, 24 mg/day, or 32 mg/day is administered in divided doses, twice a day (e.g., a 16 mg/day dose is administered as 8 mg twice daily, or a 24 mg/day does is administered as 12 mg twice daily). In another embodiment, a dose of 8 mg/day, 16 mg/day, 24 mg/day, or 32 mg/day is administered in divided doses, twice a day (e.g., a 32 mg/day dose is administered as 16 mg of Compound (I) (either as the free base, or as an equivalent amount of a pharmaceutically acceptable salt, such as the phosphate salt) twice daily, i.e., in separate doses. In one specific embodiment, a dose of 16 mg/day is administered as 8 mg of Compound (I) (either as the free base, or as an equivalent amount of a pharmaceutically acceptable salt, such as the phosphate salt) twice daily, i.e., in separate doses. It will be understood that reference to an amount of Compound (I), or a pharmaceutically acceptable salt thereof, includes an amount of a pharmaceutically acceptable salt of Compound (I) (such as the phosphate salt) which is equivalent to the stated amount of Compound (I) as the free base (e.g., 10.5 mg of Compound (I) phosphate salt is equivalent to 8 mg of Compound (I) free base).

In certain embodiments, an effective amount of Compound (I), or a pharmaceutically acceptable salt thereof is about 4 mg (such as 4 mg) twice per day. In a specific embodiment, an effective amount of Compound (I) is administered as about 5.3 mg (such as 5.3 mg) of the phosphate salt of Compound (I) twice per day. In certain embodiments, an effective amount of Compound (I), or a pharmaceutically acceptable salt thereof is about 8 mg (such as 8 mg) twice per day. In a specific embodiment, Compound (I) is administered as about 10.5 mg (such as 10.5 mg) of the phosphate salt of Compound (I) twice per day.

In certain embodiments, an effective amount of Compound (I), or a pharmaceutically acceptable salt thereof is about 12 mg (such as 12 mg) twice per day. In a specific embodiment, effective amount of Compound (I) is about 15.8 mg (such as 15.8 mg) of the phosphate salt of Compound (I) twice per day. In certain embodiments, an effective amount of Compound (I), or a pharmaceutically acceptable salt thereof is about 16 mg (such as 16 mg) twice per day. In a specific embodiment, the effective amount of Compound (I) is about 21.1 mg (such as 21.1 mg) of the phosphate salt of Compound (I) twice per day.

EXAMPLES

Example 1—Human Studies—Phase 2a

A Phase 2a trial was conducted to evaluate the safety and efficacy of Compound (I) (CTP-543) in subjects with alopecia, with the primary efficacy analysis at week 24. The Phase 2a trial was a double-blind, randomized, placebo-controlled trial to evaluate the safety and efficacy of Compound (I) in adult patients with moderate-to-severe alopecia areata. Patients were sequentially randomized to receive one of three doses of Compound I as the phosphate salt (e.g., 10.5 mg of Compound (I) phosphate salt is equivalent to 8 mg of Compound (I) free base). The doses of Compound (I) were 4, 8 (i.e., about 10.5 mg of Compound (I) phosphate salt), and 12 mg twice daily, and there was also a patient group receiving placebo. The primary outcome measure utilized the severity of alopecia tool (SALT) after 24 weeks of dosing.

Interim top line analysis for the 4 mg, 8 mg, and 12 mg cohorts is discussed below. The primary endpoint for the study was a 50% relative reduction in SALT between Week 24 and baseline.

The demographics of the subjects enrolled in the trial and receiving 4, 8, or 12 mg (twice daily) or placebo are shown in Table 1 below:

TABLE 1

| | Placebo | CTP-543 4 mg | CTP-543 8 mg | CTP-543 12 mg |
|---|---|---|---|---|
| Number of Randomized Patients | 44 | 30 | 38 | 37 |
| Efficacy Population | 43 | 28 | 38 | 36 |
| Age: Mean (SD) | 38 (14) | 36 (11) | 37 (14) | 36 (12) |
| Males, N (%) | 15 (34) | 8 (27) | 12 (32) | 9 (24) |
| Females, N (%) | 29 (66) | 22 (73) | 26 (68) | 28 (76) |
| Race: N (%) | | | | |
| White | 33 (75) | 25 (83) | 26 (68) | 30 (81) |
| Black or African American | 7 (14) | 2 (7) | 7 (18) | 3(8) |
| Asian | 2 (4.5) | 2 (7) | 2 (5) | 4 (11) |
| Other | 2 (4.5) | 1 (3) | 3 (8) | 0 (0) |

The baseline characteristics of the subjects are shown in Table 2 below:

TABLE 2

| | Placebo | CTP-543 4 mg | CTP-543 8 mg | CTP-543 12 mg |
|---|---|---|---|---|
| Episode Duration: Yr, Mean | 4.1 | 6 | 3.8 | 3.5 |
| SALT score, Mean (SD) | 86.8 (18.4) | 88.7 (16.2) | 89.1 (16.4) | 87.3 (18.7) |
| AA Patchy, N (%) | 21 (47.7) | 16 (53.3) | 16 (42.1) | 16 (43.2) |
| AA Totalis, N (%) | 6 (13.6) | 2 (6.7) | 6 (15.8) | 8 (21.6) |
| AA Universalis, N (%) | 17 (38.6) | 12 (40.0) | 14 (36.8) | 10 (27.0) |
| AA Ophiasis, N (%) | 0 (0) | 0 (0) | 2 (5.3) | 3 (8.1) |

The most common treatment emergent adverse events by patient (≥10%) are shown in Table 3 below:

TABLE 3

| Preferred Term | Placebo | CTP-543 4 mg | CTP-543 8 mg | CTP-543 12 mg |
|---|---|---|---|---|
| Headache | 4 (9.1%) | 5 (17.2%) | 10 (26.3%) | 7 (19.4%) |
| Nausea | 4 (9.1%) | 4 (13.8%) | 4 (10.5%) | 1 (2.8%) |
| Acne | 2 (4.5%) | 4 (13.8%) | 4 (10.5%) | 6 (16.7%) |
| Cough | 0 | 4 (13.8%) | 1 (2.6%) | 2 (5.6%) |
| Diarrhoea | 3 (6.8%) | 3 (10.3%) | 1 (2.6%) | 0 |
| Nasopharyngitis | 1 (2.3%) | 3 (10.3%) | 3 (7.9%) | 9 (25.0%) |
| Folliculitis | 0 | 3 (10.3%) | 2 (5.3%) | 1 (2.8%) |
| Blood creatine phosphokinase increased | 1 (2.3%) | 3 (10.3%) | 2 (5.3%) | 1 (2.8%) |

TABLE 3-continued

| Preferred Term | Placebo | CTP-543 4 mg | CTP-543 8 mg | CTP-543 12 mg |
|---|---|---|---|---|
| Oroharyngeal pain | 1 (2.3%) | 3 (10.3%) | 2 (5.3%) | 1 (2.8%) |
| Upper respiratory tract infection | 7 (15.9%) | 2 (6.9%) | 2 (5.3%) | 7 (19.4%) |
| LDL increase | 0 | 0 | 4 (10.5%) | 0 |

No serious adverse events were reported. In the preliminary analysis of the placebo, 4 mg, and 8 mg groups, there were only 3 Grade 3/4 hematology events, distributed equally across the placebo, 4 mg, and 8 mg groups.

In conclusion, the primary efficacy endpoint of the study was met. 58% of patients treated with 12 mg BID (twice daily) and 47% of patients treated with 8 mg BID (twice daily) of CTP-543 achieved a ≥50% reduction in their overall SALT score compared to 8.6% placebo ($p<0.001$). In addition, 42% of patients treated with 12 mg BID ($p<0.001$) and 29% of patients treated with 8 mg BID ($p<0.05$) of CTP-543 achieved a ≥75% reduction in their overall SALT score compared to 7% placebo. Further, 36% of patients treated with 12 mg BID ($p<0.001$) and 16% of patients treated with 8 mg BID ($p<0.05$) of CTP-543 achieved a ≥90% reduction in their overall SALT score compared to 2% placebo. 21% of patients treated with 4 mg BID of CTP-543 achieved a ≥50% reduction in their overall SALT score compared to 8.6% placebo (not significant). The 12 mg BID and 8 mg BID dose groups were significantly different than the 4 mg BID dose group ($p<0.05$). Significant changes in SALT score were observed starting at 12 weeks for the 12 mg and 8 mg cohorts compared to placebo ($p<0.05$).

Treatment was generally well-tolerated with no serious adverse events. The 4 mg BID dose failed to separate from placebo on all measures. The 8 mg BID dose and 12 mg BID doses were significantly different from placebo on all SALT measures at week 24, the conclusion of the trial. The 12 mg BID dose was numerically superior and generally produced faster onset and greater effect compared to the 8 mg BID dose.

Example 2—Open-Label Extension Study

Figure 8:
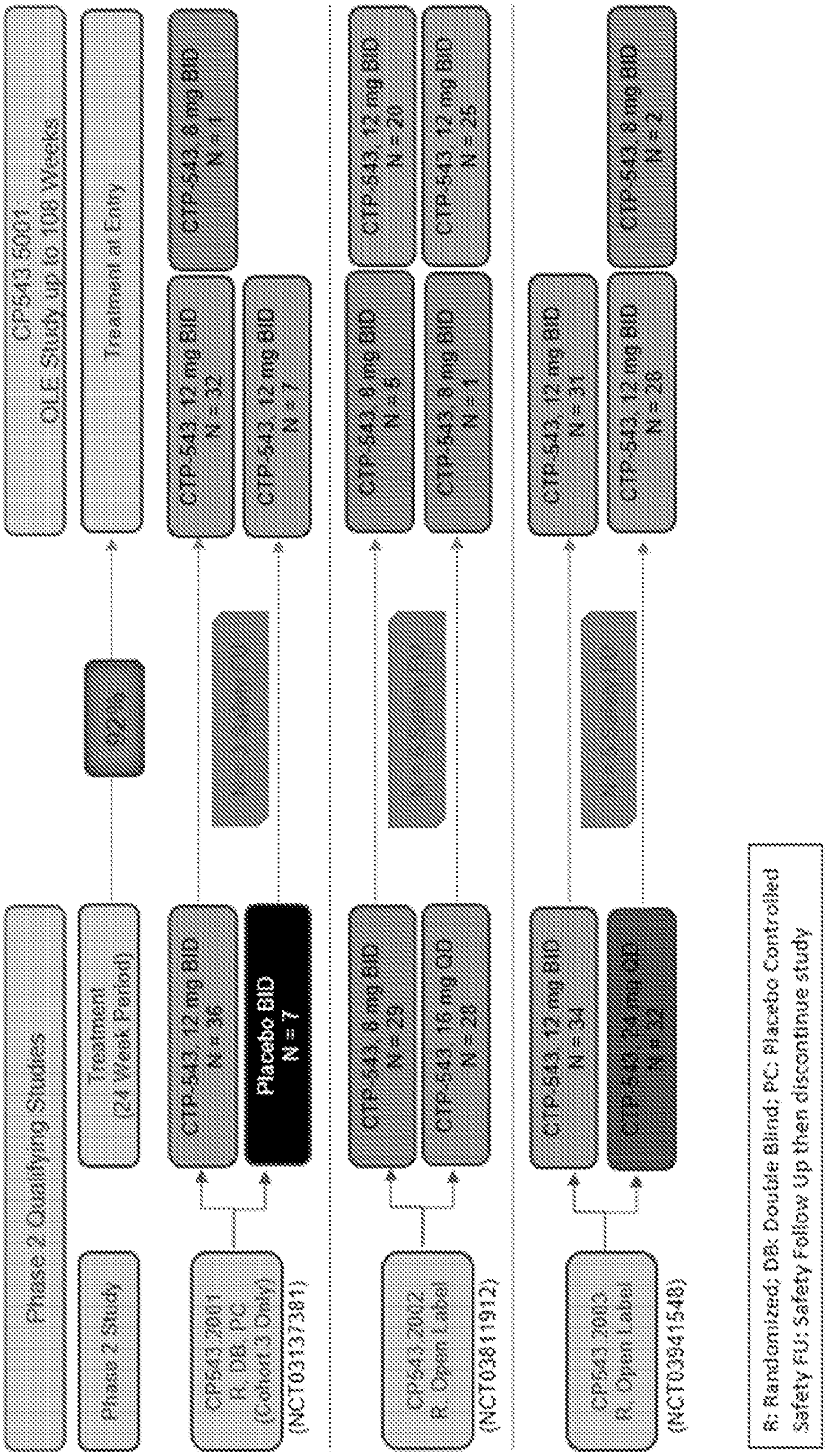
FIG. 8 shows the patient entry and disposition of subjects in an open-label extension (OLE) study of Compound (I) (CTP-543).

In an ongoing open-label extension study, subjects who were previously enrolled in a qualifying clinical study (including the study described in Example 1) and received either a total daily dose of 16 mg of Compound (I) (CTP-543, phosphate salt), a total daily dose of 24 mg of CTP-543, or placebo, and completed through the 24-week treatment period, were eligible to enroll in an open-label extension study (OLE) and continue to receive treatment with CTP-543 phosphate. A total of 152 subjects were enrolled in the OLE. In the OLE, subjects received daily treatment with CTP-543 at a dose of 8 mg BID or 12 mg BID (see FIG. 8). Dose adjustments were allowed at the investigator's discretion. One subject enrolled in the OLE, who received a daily dose of 24 mg QD of CTP-543 for approximately 9 months (i.e., the 24-week study period and the initial 3 months of the OLE), experienced hair growth at that dose (SALT score of zero, i.e., full regrowth of hair prior to dose reduction). The subject then had their dose reduced to a daily dose of 8 mg BID of CTP-543 phosphate. After approximately 7 months in the OLE receiving the lower daily dose of 8 mg BID of CTP-543, the subject continued to substantially maintain hair regrowth, with a SALT score of 7.92.

Example 3—Phase 2 Durability Study

A Phase 2 clinical trial is conducted as a two part, double-blind, randomized, multicenter study to evaluate the regrowth of hair after treatment with Compound (I) (CTP-543), and subsequent durability of that regrowth following dose reduction or drug discontinuation in adult patients with moderate to severe alopecia areata. Patients are between 18 and 65 years of age and experiencing an episode of hair loss associated with alopecia areata lasting at least 6 months and not exceeding 10 years. Patients not currently being treated for alopecia areata or with other treatments that might affect hair regrowth or immune response must have at least 50% hair loss as measured by the Severity of Alopecia Tool (SALT) at Screening and Baseline. Up to approximately 75% of patients with complete or near complete (SALT≥95) hair loss are enrolled.

The study is divided into 2 Parts:

Part A: Period 1 (Treatment Phase) and Period 2 (Dose Modification Phase)

Part B: Re-Treatment Phase

Part A: Period 1

Part A, Period 1 is a double-blind Treatment Period where approximately 200 or 300 patients are randomized to receive one of two doses of Compound (I) (CTP-543) as the phosphate salt (e.g., 10.5 mg of Compound (I) phosphate salt is equivalent to 8 mg of Compound (I) free base) for 24 weeks. The doses are either 8 mg twice a day (BID) of Compound (I) (i.e., about 10.5 mg of Compound (I) phosphate salt), or 12 mg BID of Compound (I) (i.e., about 15.8 mg of Compound (I) phosphate salt). Randomization is stratified by scalp hair loss into one of the following two categories: 1) Partial scalp hair loss (SALT≥50 and <95); 2) complete or near-complete scalp hair loss (SALT≥95). Patients take the first dose of study drug in the clinic on Day 1 and are instructed to take study drug daily approximately every 12 hours for the duration of Period 1. Other baseline assessments for Part A, Period 1 include Patient and Clinician Global Impression of disease Severity (CGI-S and PGI-S), and Patient Reported Outcome for Satisfaction (SPRO) and Hair Quality (QPRO). Blood samples for pharmacokinetic assessment are taken periodically. Photographs of the scalp are also taken to provide a visual record at the time of SALT assessment and are performed at additional select visits throughout the study. The primary efficacy analysis to determine the Responders for each dose group is conducted when all patients have completed Week 24 from Part A, Period 1. In some embodiments, at End of Treatment (EOT) for Part A, Period 1, patients having a <50% change in their SALT score from Baseline are defined as a non-responder and have the opportunity to continue receiving treatment in an Open-Label Extension study, or they can complete treatment at Week 24 and return in 4 weeks for the Post-Treatment Safety Follow-up.

In some embodiments, patients from each dose group having a ≥50% change in their SALT score from Baseline at Week 24 are defined as a responder and enter Part A, Period 2.

In some embodiments, at End of Treatment (EOT) for Part A, Period 1, treatment success (Responders) are defined as patients from each dose group having a SALT score of ≤20 at Week 24. These Responders enter Part A, Period 2 of the study. Patients having a SALT score >20 are defined as a Non-Responder and have the opportunity to continue receiving treatment in the Open-Label Extension study or they complete treatment at Week 24 and return in 4 weeks for the Post-Treatment Safety Follow-up.

Part A, Period 1 (Treatment Phase) lasts 24 weeks. Assessment of treatment response using SALT for efficacy occurs at 4, 8, 12, 16, 20 and 24 weeks.

Part A: Period 2

Figure 7:
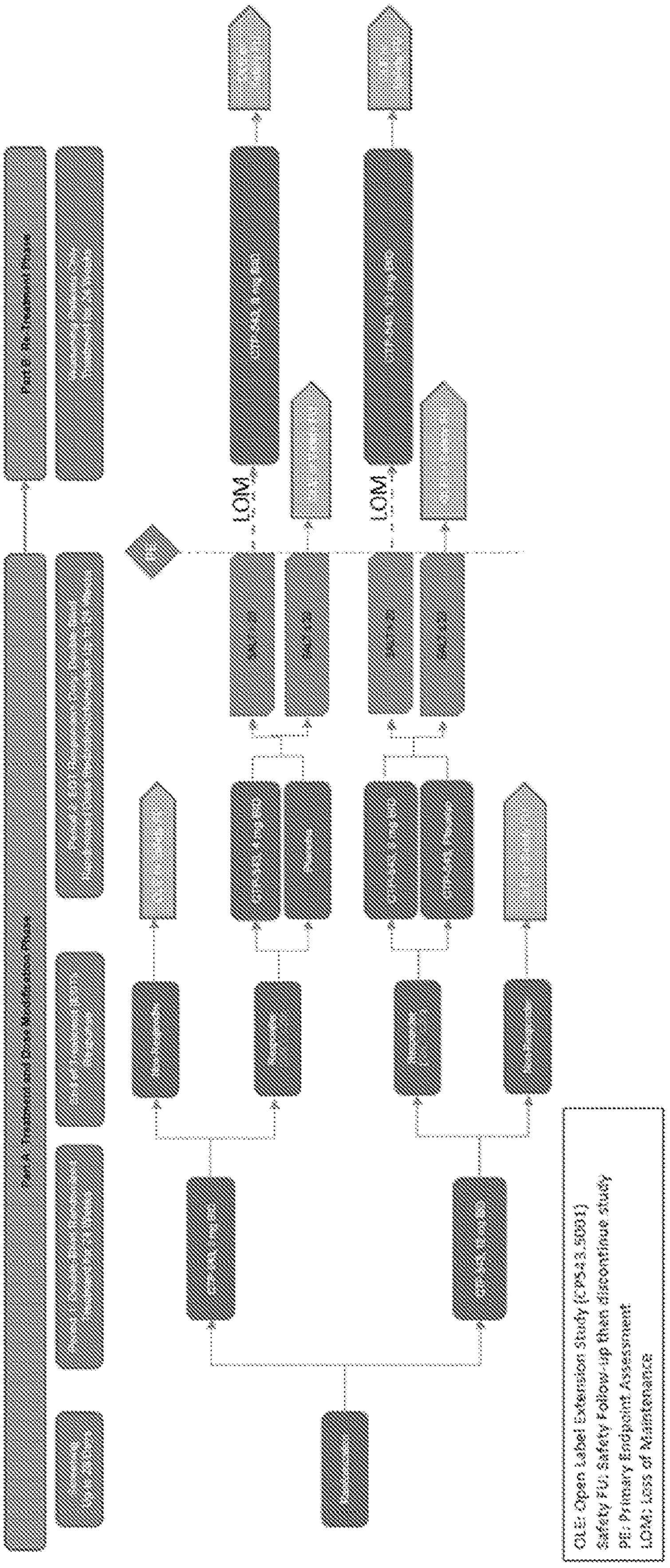
FIG. 7 shows the design of a study for administration of 8 mg BID or 12 mg BID of Compound (I) (CTP-543) for a first period, followed by a second period of administration of a lower dose of Compound (I) or placebo.

In Part A, Period 2, patients are re-randomized to receive either a lower dose of Compound (I) (4 mg BID for patients previously receiving 8 mg BID or 8 mg BID for patients previously receiving 12 mg BID) or placebo. Patients in Part A, Period 2 stay on the assigned dose for a maximum of 24 weeks or until they meet the criteria for loss of regrowth maintenance (LOM). The criteria for LOM is a SALT score greater than 20. Any patient meeting the LOM criteria at any assessment timepoint during Part A, Period 2 enters Part B of the study and returns to their original Compound (I) treatment from Part A, Period 1 (8 mg BID or 12 mg BID). Patients not meeting the LOM criteria (i.e., patients having a SALT score of less than or equal to 20) at the end of 24 weeks have the opportunity to continue receiving treatment in the Open-Label Extension study at their original Part A, Period 1 dose, or they can complete treatment at Week 24 and return in 4 weeks for the Post-Treatment Safety Follow-up. The study design is depicted in FIG. 7.

Part A, Period 2 (Dose Modification) lasts up to 24 weeks or until the patient meets the criteria for LOM. Assessment of treatment response using SALT for efficacy occurs monthly until the criteria for LOM is met or the 24-week period is complete.

Part B

Any patient from Part A, Period 2 meeting the LOM criteria (SALT>20) enters into Part B of the study and returns to their original 8 mg BID or 12 mg BID dose from Part A, Period 1. In some embodiments, patients stay on their assigned doses for 24 weeks regardless of whether they meet the criteria for Restoration of Regrowth (ROR) or not. In some embodiments, Patients stay on their assigned dose for 24 weeks or until they meet the criteria for Restoration of Regrowth (ROR). In some embodiments, ROR is defined as the patient's attainment of a SALT score ≤their original EOT SALT score at the end of Part A, Period 1. In some embodiments, ROR is defined as the patient's attainment of a SALT score of ≤20. In some embodiments, any patient meeting the ROR criteria at any assessment timepoint during Part B exits the study and is eligible to enroll in the Open-Label Extension study. Assessment of treatment response using SALT for efficacy will occur monthly until the criteria for Restoration of Regrowth (ROR) is met or the 24-week period is complete. Patients not meeting the ROR criteria have the opportunity to continue receiving treatment in the Open-Label Extension study, or they can complete treatment at Week 24 and return in 4 weeks for the Post-Treatment Safety Follow-up.

Without further description, it is believed that one of ordinary skill in the art can, using the preceding description and the illustrative examples, make and utilize the compounds of the present invention and practice the claimed methods. It should be understood that the foregoing discussion and examples merely present a detailed description of certain preferred embodiments. It will be apparent to those of ordinary skill in the art that various modifications and equivalents can be made without departing from the spirit and scope of the invention.

What is claimed is:

1. A method of treating a hair loss disorder in a human subject, the method comprising administering to the subject a compound represented by the following structural formula:

Compound (I)

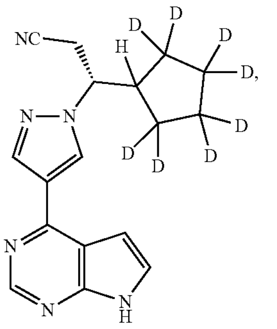

or a pharmaceutically acceptable salt thereof;

wherein each position designated specifically as deuterium has at least 95% incorporation of deuterium;

wherein the compound, or pharmaceutically acceptable salt thereof, is administered for (1) a first period of 8-24 weeks in an amount in the range of about 8 mg to about 32 mg per day, followed by (2) a second period of at least 8 weeks wherein the compound, or pharmaceutically acceptable salt thereof, is administered in an amount per day that is 50 to 75 percent of the amount per day administered during the first period, such that the hair loss disorder is treated.

2. The method of claim 1, wherein the hair loss disorder is alopecia areata.

3. The method of claim 1, wherein, in the first period, the compound, or a pharmaceutically acceptable salt thereof, is administered at about 16 mg/day, about 24 mg/day, or about 32 mg per day.

4. The method of claim 1, wherein, in the second period, the compound, or a pharmaceutically acceptable salt thereof, is administered at about 8 mg/day, about 12 mg/day, or about 16 mg per day.

5. The method of claim 1, wherein in the first period, the compound, or a pharmaceutically acceptable salt thereof, is administered at about 24 mg/day, and in the second period, the compound, or a pharmaceutically acceptable salt thereof, is administered at about 16 mg/day.

6. The method of claim 5, wherein the about 24 mg/day of the compound or salt thereof is administered once per day, and the about 16 mg/day is administered once per day.

7. The method of claim 5, wherein the about 24 mg/day of the compound or salt thereof is administered as about 12 mg twice per day, and the about 16 mg/day of the compound or salt thereof is administered as about 8 mg twice per day.

8. The method of claim 1, wherein in the first period, the compound, or a pharmaceutically acceptable salt thereof, is administered at about 16 mg/day, and in the second period, the compound, or a pharmaceutically acceptable salt thereof, is administered at about 8 mg/day.

9. The method of claim 1, wherein the compound, or a pharmaceutically acceptable salt thereof, is administered orally.

10. The method of claim 1, wherein the compound, or a pharmaceutically acceptable salt thereof, is administered in a pharmaceutical formulation which is a tablet.

11. The method of claim 1, wherein the compound, or a pharmaceutically acceptable salt thereof, is administered once per day in the first period.

12. The method of claim 1, wherein the compound, or a pharmaceutically acceptable salt thereof, is administered twice per day in the first period.

13. The method of claim 1, wherein the first period is about 8-12 weeks.

14. The method of claim 1, wherein the first period is about 24 weeks.

15. The method of claim 1, wherein the second period is at least 12 weeks.

16. The method of claim 1, wherein the second period is at least 24 weeks.

17. The method of claim 1, wherein in Compound (I), each position designated specifically as deuterium has at least 97% incorporation of deuterium.

18. The method of claim 1, wherein the subject experiences a ≥50% decrease in SALT score at the end of the first period relative to the subject's baseline SALT score prior to treatment.

19. The method of claim 1, wherein the subject's SALT score is less than or equal to 20 at the end of the second period.

20. The method of claim 1, wherein the subject's SALT score is less than or equal to 20 at the end of the first period.

* * * * *